United States Patent
Budiman

(10) Patent No.: US 11,896,371 B2
(45) Date of Patent: Feb. 13, 2024

(54) METHOD AND APPARATUS FOR IMPROVING LAG CORRECTION DURING IN VIVO MEASUREMENT OF ANALYTE CONCENTRATION WITH ANALYTE CONCENTRATION VARIABILITY AND RANGE DATA

(71) Applicant: ABBOTT DIABETES CARE INC., Alameda, CA (US)

(72) Inventor: Erwin Satrya Budiman, Fremont, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 38 days.

(21) Appl. No.: 17/073,852

(22) Filed: Oct. 19, 2020

(65) Prior Publication Data
US 2021/0030334 A1 Feb. 4, 2021

Related U.S. Application Data

(63) Continuation of application No. 15/910,927, filed on Mar. 2, 2018, now Pat. No. 10,842,420, which is a (Continued)

(51) Int. Cl.
*A61B 5/00* (2006.01)
*A61B 5/145* (2006.01)
(Continued)

(52) U.S. Cl.
CPC ...... *A61B 5/14532* (2013.01); *A61B 5/14503* (2013.01); *A61B 5/14546* (2013.01); (Continued)

(58) Field of Classification Search
CPC ............ A61B 5/14503; A61B 5/14532; A61B 5/14546; A61B 5/7275; A61B 5/7203; A61B 5/7235
See application file for complete search history.

(56) References Cited

U.S. PATENT DOCUMENTS 3,581,062 A   5/1971   Aston
3,926,760 A   12/1975  Allen et al.
(Continued)

FOREIGN PATENT DOCUMENTS

CA   2468577   6/2003
CA   2678336   5/2008
(Continued)

OTHER PUBLICATIONS

U.S. Appl. No. 16/902,111 (US 2020/0305803), filed Jun. 15, 2020 (Oct. 1, 2020).
(Continued)

*Primary Examiner* — Eric F Winakur
(74) *Attorney, Agent, or Firm* — Baker Botts L.LP.

(57) ABSTRACT

Methods, devices, and systems are provided for correcting lag in measurements of analyte concentration level in interstitial fluid. The invention includes receiving a signal representative of sensor data from an analyte monitoring system related to an analyte level measured over time, computing rates of change of the sensor data for a time period of the sensor data, computing a rate distribution of the rates of change, transforming the rate distribution into a linear arrangement, determining a best-fit line for the transformed rate distribution, computing a slope of the best-fit line; and using the slope of the best-fit line as a representation of a variability of the analyte level to adjust an amount of lag correction applied to the sensor data. Numerous additional features are disclosed.

23 Claims, 8 Drawing Sheets

Related U.S. Application Data continuation of application No. 14/431,168, filed as application No. PCT/US2013/060471 on Sep. 18, 2013, now Pat. No. 9,907,492.

(60) Provisional application No. 61/705,929, filed on Sep. 26, 2012.

(51) Int. Cl.
  *G06K 9/00* (2022.01)
  *G16H 50/20* (2018.01)

(52) U.S. Cl.
  CPC .......... *A61B 5/7203* (2013.01); *A61B 5/7235* (2013.01); *A61B 5/7275* (2013.01); *G16H 50/20* (2018.01); *A61B 2560/0475* (2013.01); *G06F 2218/10* (2023.01)

(56) References Cited

U.S. PATENT DOCUMENTS

| | | |
|---|---|---|
| 3,949,388 A | 4/1976 | Fuller |
| 3,960,497 A | 6/1976 | Acord et al. |
| 3,978,856 A | 9/1976 | Michel |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,441,968 A | 4/1984 | Emmer et al. |
| 4,462,048 A | 7/1984 | Ross |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,619,793 A | 10/1986 | Lee |
| 4,671,288 A | 6/1987 | Gough |
| 4,703,756 A | 11/1987 | Gough et al. |
| 4,711,245 A | 12/1987 | Higgins et al. |
| 4,731,051 A | 3/1988 | Fischell |
| 4,731,726 A | 3/1988 | Allen, III |
| 4,749,985 A | 6/1988 | Corsberg |
| 4,750,496 A | 6/1988 | Reinhart et al. |
| 4,757,022 A | 7/1988 | Shults et al. |
| 4,759,366 A | 7/1988 | Callaghan |
| 4,777,953 A | 10/1988 | Ash et al. |
| 4,779,618 A | 10/1988 | Mund et al. |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,947,845 A | 8/1990 | Davis |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,034,112 A | 7/1991 | Murase et al. |
| 5,050,612 A | 9/1991 | Matsumura |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,089,112 A | 2/1992 | Skotheim et al. |
| 5,106,365 A | 4/1992 | Hernandez |
| 5,113,869 A | 5/1992 | Nappholz et al. |
| 5,122,925 A | 6/1992 | Inpyn |
| 5,135,004 A | 8/1992 | Adams et al. |
| 5,145,381 A | 9/1992 | Volz |
| 5,148,812 A | 9/1992 | Verrier et al. |
| 5,165,407 A | 11/1992 | Wilson et al. |
| 5,199,428 A | 4/1993 | Obel et al. |
| 5,202,261 A | 4/1993 | Musho et al. |
| 5,203,326 A | 4/1993 | Collins |
| 5,204,264 A | 4/1993 | Kaminer et al. |
| 5,210,778 A | 5/1993 | Massart |
| 5,231,988 A | 8/1993 | Wernicke et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,103 A | 11/1993 | Yoshioka et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,313,953 A | 5/1994 | Yomtov et al. |
| 5,320,715 A | 6/1994 | Berg |
| 5,320,725 A | 6/1994 | Gregg et al. |
| 5,322,063 A | 6/1994 | Allen et al. |
| 5,328,460 A | 7/1994 | Lord et al. |
| 5,330,634 A | 7/1994 | Wong et al. |
| 5,340,722 A | 8/1994 | Wolfbeis et al. |
| 5,342,789 A | 8/1994 | Chick et al. |
| 5,352,351 A | 10/1994 | White et al. |
| 5,356,786 A | 10/1994 | Heller et al. |
| 5,360,404 A | 11/1994 | Novacek et al. |
| 5,365,426 A | 11/1994 | Siegel et al. |
| 5,372,427 A | 12/1994 | Padovani et al. |
| 5,376,070 A | 12/1994 | Purvis et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,400,795 A | 3/1995 | Murphy et al. |
| 5,408,999 A | 4/1995 | Singh et al. |
| 5,410,326 A | 4/1995 | Goldstein |
| 5,411,647 A | 5/1995 | Johnson et al. |
| 5,425,749 A | 6/1995 | Adams |
| 5,425,868 A | 6/1995 | Pedersen |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,520,191 A | 5/1996 | Karlsson et al. |
| 5,531,878 A | 7/1996 | Vadgama et al. |
| 5,532,686 A | 7/1996 | Urbas et al. |
| 5,543,326 A | 8/1996 | Heller et al. |
| 5,552,997 A | 9/1996 | Massart |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,890 A | 5/1997 | Carter et al. |
| 5,634,468 A | 6/1997 | Platt et al. |
| 5,640,954 A | 6/1997 | Pfeiffer et al. |
| 5,653,239 A | 8/1997 | Pompei et al. |
| 5,660,163 A | 8/1997 | Schulman et al. |
| 5,665,222 A | 9/1997 | Heller et al. |
| 5,695,623 A | 12/1997 | Michel et al. |
| 5,707,502 A | 1/1998 | McCaffrey et al. |
| 5,711,001 A | 1/1998 | Bussan et al. |
| 5,711,861 A | 1/1998 | Ward et al. |

(56) References Cited

U.S. PATENT DOCUMENTS

| | | |
|---|---|---|
| 5,720,295 A | 2/1998 | Greenhut et al. |
| 5,724,030 A | 3/1998 | Urbas et al. |
| 5,733,259 A | 3/1998 | Valcke et al. |
| 5,735,285 A | 4/1998 | Albert et al. |
| 5,741,211 A | 4/1998 | Renirie et al. |
| 5,749,907 A | 5/1998 | Mann |
| 5,772,586 A | 6/1998 | Heinonen et al. |
| 5,785,660 A | 7/1998 | van Lake et al. |
| 5,791,344 A | 8/1998 | Schulman et al. |
| 5,792,065 A | 8/1998 | Xue et al. |
| 5,804,047 A | 9/1998 | Karube et al. |
| 5,820,551 A | 10/1998 | Hill et al. |
| 5,822,715 A | 10/1998 | Worthington et al. |
| 5,863,400 A | 1/1999 | Drummond et al. |
| 5,891,047 A | 4/1999 | Lander et al. |
| 5,891,049 A | 4/1999 | Cyrus et al. |
| 5,899,855 A | 5/1999 | Brown |
| 5,914,026 A | 6/1999 | Blubaugh, Jr. et al. |
| 5,918,603 A | 7/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,960,797 A | 10/1999 | Kramer et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,995,860 A | 11/1999 | Sun et al. |
| 6,001,067 A | 12/1999 | Shults et al. |
| 6,016,443 A | 1/2000 | Ekwall et al. |
| 6,021,350 A | 2/2000 | Mathson |
| 6,024,699 A | 2/2000 | Surwit et al. |
| 6,038,469 A | 3/2000 | Karlsson et al. |
| 6,049,727 A | 4/2000 | Crothall |
| 6,071,391 A | 6/2000 | Gotoh et al. |
| 6,073,031 A | 6/2000 | Helstab et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,103,033 A | 8/2000 | Say et al. |
| 6,108,577 A | 8/2000 | Benser |
| 6,112,116 A | 8/2000 | Fischell |
| 6,115,622 A | 9/2000 | Minoz |
| 6,115,628 A | 9/2000 | Stadler et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,128,526 A | 10/2000 | Stadler et al. |
| 6,130,623 A | 10/2000 | MacLellan et al. |
| 6,134,461 A | 10/2000 | Say et al. |
| 6,143,164 A | 11/2000 | Heller et al. |
| 6,144,837 A | 11/2000 | Quy |
| 6,144,871 A | 11/2000 | Saito et al. |
| 6,159,147 A | 12/2000 | Lichter et al. |
| 6,161,095 A | 12/2000 | Brown |
| 6,162,611 A | 12/2000 | Heller et al. |
| 6,168,957 B1 | 1/2001 | Matzinger et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,212,417 B1 | 4/2001 | Ikeda et al. |
| 6,219,574 B1 | 4/2001 | Cormier et al. |
| 6,223,283 B1 | 4/2001 | Chaiken et al. |
| 6,233,471 B1 | 5/2001 | Berner et al. |
| 6,233,486 B1 | 5/2001 | Ekwall et al. |
| 6,237,394 B1 | 5/2001 | Harris et al. |
| 6,248,067 B1 | 6/2001 | Causey, III et al. |
| 6,249,705 B1 | 6/2001 | Snell |
| 6,254,586 B1 | 7/2001 | Mann et al. |
| 6,256,538 B1 | 7/2001 | Ekwall |
| 6,264,606 B1 | 7/2001 | Ekwall et al. |
| 6,270,455 B1 | 8/2001 | Brown |
| 6,272,379 B1 | 8/2001 | Fischell et al. |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,361,503 B1 | 3/2002 | Starobin et al. |
| 6,366,794 B1 | 4/2002 | Moussy et al. |
| 6,368,141 B1 | 4/2002 | VanAntwerp et al. |
| 6,377,828 B1 | 4/2002 | Chaiken et al. |
| 6,377,852 B1 | 4/2002 | Bornzin et al. |
| 6,377,894 B1 | 4/2002 | Deweese et al. |
| 6,379,301 B1 | 4/2002 | Worthington et al. |
| 6,381,493 B1 | 4/2002 | Stadler et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,461,496 B1 | 10/2002 | Feldman et al. |
| 6,471,689 B1 | 10/2002 | Joseph et al. |
| 6,475,372 B1 | 11/2002 | Ohara et al. |
| 6,475,750 B1 | 11/2002 | Han et al. |
| 6,478,736 B1 | 11/2002 | Mault |
| 6,484,046 B1 | 11/2002 | Say et al. |
| 6,496,729 B2 | 12/2002 | Thompson |
| 6,497,655 B1 | 12/2002 | Linberg et al. |
| 6,498,043 B1 | 12/2002 | Schulman et al. |
| 6,501,983 B1 | 12/2002 | Natarajan et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,520,326 B2 | 2/2003 | McIvor et al. |
| 6,522,903 B1 | 2/2003 | Berman et al. |
| 6,540,891 B1 | 4/2003 | Stewart et al. |
| 6,544,212 B2 | 4/2003 | Galley et al. |
| 6,549,796 B2 | 4/2003 | Sohrab |
| 6,551,494 B1 | 4/2003 | Heller et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,565,509 B1 | 5/2003 | Say et al. |
| 6,572,542 B1 | 6/2003 | Houben et al. |
| 6,574,490 B2 | 6/2003 | Abbink et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,587,704 B1 | 7/2003 | Fine et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |

(56) References Cited

U.S. PATENT DOCUMENTS

| | | |
|---|---|---|
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,622,045 B2 | 9/2003 | Snell et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciuczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,721,582 B2 | 4/2004 | Trepagnier et al. |
| 6,730,200 B1 | 5/2004 | Stewart et al. |
| 6,731,976 B2 | 5/2004 | Penn et al. |
| 6,731,985 B2 | 5/2004 | Poore et al. |
| 6,733,446 B2 | 5/2004 | Lebel et al. |
| 6,735,183 B2 | 5/2004 | O'Toole et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,770,030 B1 | 8/2004 | Schaupp et al. |
| 6,773,671 B1 | 8/2004 | Lewis et al. |
| 6,790,178 B1 | 9/2004 | Mault et al. |
| 6,804,558 B2 | 10/2004 | Haller et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,835,553 B2 | 12/2004 | Han et al. |
| 6,850,790 B2 | 2/2005 | Berner et al. |
| 6,850,859 B1 | 2/2005 | Schuh |
| 6,862,465 B2 | 3/2005 | Shults et al. |
| 6,865,407 B2 | 3/2005 | Kimball et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,912,413 B2 | 6/2005 | Rantala et al. |
| 6,923,763 B1 | 8/2005 | Kovatchev et al. |
| 6,923,764 B2 | 8/2005 | Aceti et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman, IV et al. |
| 6,954,662 B2 | 10/2005 | Freger et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,009,511 B2 | 3/2006 | Mazar et al. |
| 7,010,345 B2 | 3/2006 | Hill et al. |
| 7,011,630 B2 | 3/2006 | Desai et al. |
| 7,016,713 B2 | 3/2006 | Gardner et al. |
| 7,016,720 B2 | 3/2006 | Kroll |
| 7,020,508 B2 | 3/2006 | Stivoric et al. |
| 7,022,072 B2 | 4/2006 | Fox et al. |
| 7,022,219 B2 | 4/2006 | Mansouri et al. |
| 7,024,236 B2 | 4/2006 | Ford et al. |
| 7,024,245 B2 | 4/2006 | Lebel et al. |
| 7,025,425 B2 | 4/2006 | Kovatchev et al. |
| 7,027,848 B2 | 4/2006 | Robinson et al. |
| 7,029,443 B2 | 4/2006 | Kroll |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,043,305 B2 | 5/2006 | KenKnight et al. |
| 7,052,472 B1 | 5/2006 | Miller et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,074,307 B2 | 7/2006 | Simpson et al. |
| 7,076,300 B1 | 7/2006 | Kroll et al. |
| 7,081,195 B2 | 7/2006 | Simpson et al. |
| 7,082,334 B2 | 7/2006 | Boute et al. |
| 7,092,891 B2 | 8/2006 | Maus et al. |
| 7,096,064 B2 | 8/2006 | Deno et al. |
| 7,098,803 B2 | 8/2006 | Mann et al. |
| 7,103,412 B1 | 9/2006 | Kroll |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,125,382 B2 | 10/2006 | Zhou et al. |
| 7,134,999 B2 | 11/2006 | Brauker et al. |
| 7,136,689 B2 | 11/2006 | Shults et al. |
| 7,142,911 B2 | 11/2006 | Boileau et al. |
| 7,153,265 B2 | 12/2006 | Vachon |
| 7,167,818 B2 | 1/2007 | Brown |
| 7,171,274 B2 | 1/2007 | Starkweather et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,220,387 B2 | 5/2007 | Flaherty et al. |
| 7,225,535 B2 | 6/2007 | Feldman et al. |
| 7,226,978 B2 | 6/2007 | Tapsak et al. |
| 7,228,182 B2 | 6/2007 | Healy et al. |
| 7,237,712 B2 | 7/2007 | DeRocco et al. |
| 7,258,673 B2 | 8/2007 | Racchini et al. |
| 7,267,665 B2 | 9/2007 | Steil et al. |
| 7,272,436 B2 | 9/2007 | Gill et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,295,867 B2 | 11/2007 | Berner et al. |
| 7,297,114 B2 | 11/2007 | Gill et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,318,816 B2 | 1/2008 | Bobroff et al. |
| 7,324,850 B2 | 1/2008 | Persen et al. |
| 7,335,294 B2 | 2/2008 | Heller et al. |
| 7,347,819 B2 | 3/2008 | Lebel et al. |
| 7,354,420 B2 | 4/2008 | Steil et al. |
| 7,364,592 B2 | 4/2008 | Carr Brendel et al. |
| 7,366,556 B2 | 4/2008 | Brister et al. |
| 7,379,765 B2 | 5/2008 | Petisce et al. |

(56) References Cited

U.S. PATENT DOCUMENTS

| | | |
|---|---|---|
| 7,384,397 B2 | 6/2008 | Zhang et al. |
| 7,387,010 B2 | 6/2008 | Sunshine et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,419,573 B2 | 9/2008 | Gundel |
| 7,424,318 B2 | 9/2008 | Brister et al. |
| 7,460,898 B2 | 12/2008 | Brister et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,474,992 B2 | 1/2009 | Ariyur |
| 7,491,303 B2 | 2/2009 | Sakata et al. |
| 7,492,254 B2 | 2/2009 | Bandy et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,502,644 B2 | 3/2009 | Gill et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,524,287 B2 | 4/2009 | Bharmi |
| 7,547,281 B2 | 6/2009 | Hayes et al. |
| 7,565,197 B2 | 7/2009 | Haubrich et al. |
| 7,569,030 B2 | 8/2009 | Lebel et al. |
| 7,574,266 B2 | 8/2009 | Dudding et al. |
| 7,583,990 B2 | 9/2009 | Goode, Jr. et al. |
| 7,620,438 B2 | 11/2009 | He |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,643,798 B2 | 1/2010 | Ljung |
| 7,659,823 B1 | 2/2010 | Killian et al. |
| 7,668,596 B2 | 2/2010 | Von Arx et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,711,493 B2 | 5/2010 | Bartkowiak et al. |
| 7,736,310 B2 | 6/2010 | Taub et al. |
| 7,741,734 B2 | 6/2010 | Joannopoulos et al. |
| 7,751,864 B2 | 7/2010 | Buck, Jr. |
| 7,766,829 B2 | 8/2010 | Sloan et al. |
| 7,771,352 B2 | 8/2010 | Shults et al. |
| 7,774,145 B2 | 8/2010 | Bruaker et al. |
| 7,778,680 B2 | 8/2010 | Goode, Jr. et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,826,981 B2 | 11/2010 | Goode et al. |
| 7,831,310 B2 | 11/2010 | Lebel et al. |
| 7,857,760 B2 | 12/2010 | Brister et al. |
| 7,860,574 B2 | 12/2010 | Von Arx et al. |
| 7,866,026 B1 | 1/2011 | Wang et al. |
| 7,882,611 B2 | 2/2011 | Shah et al. |
| 7,885,697 B2 | 2/2011 | Brister et al. |
| 7,899,511 B2 | 3/2011 | Shults et al. |
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,938,797 B2 | 5/2011 | Estes |
| 7,941,200 B2 | 5/2011 | Weinert et al. |
| 7,946,984 B2 | 5/2011 | Brister et al. |
| 7,955,258 B2 | 6/2011 | Goscha et al. |
| 7,970,448 B2 | 6/2011 | Shults et al. |
| 7,974,672 B2 | 7/2011 | Shults et al. |
| 7,999,674 B2 | 8/2011 | Kamen |
| 8,060,173 B2 | 11/2011 | Goode, Jr. et al. |
| 8,072,310 B1 | 12/2011 | Everhart |
| 8,090,445 B2 | 1/2012 | Ginggen |
| 8,093,991 B2 | 1/2012 | Stevenson et al. |
| 8,094,009 B2 | 1/2012 | Allen et al. |
| 8,098,159 B2 | 1/2012 | Batra et al. |
| 8,098,160 B2 | 1/2012 | Howarth et al. |
| 8,098,161 B2 | 1/2012 | Lavedas |
| 8,098,201 B2 | 1/2012 | Choi et al. |
| 8,098,208 B2 | 1/2012 | Ficker et al. |
| 8,102,021 B2 | 1/2012 | Degani |
| 8,102,154 B2 | 1/2012 | Bishop et al. |
| 8,102,263 B2 | 1/2012 | Yeo et al. |
| 8,102,789 B2 | 1/2012 | Rosar et al. |
| 8,103,241 B2 | 1/2012 | Young et al. |
| 8,103,325 B2 | 1/2012 | Swedlow et al. |
| 8,111,042 B2 | 2/2012 | Bennett |
| 8,115,488 B2 | 2/2012 | McDowell |
| 8,116,681 B2 | 2/2012 | Baarman |
| 8,116,683 B2 | 2/2012 | Baarman |
| 8,116,837 B2 | 2/2012 | Huang |
| 8,117,481 B2 | 2/2012 | Anselmi et al. |
| 8,120,493 B2 | 2/2012 | Burr |
| 8,124,452 B2 | 2/2012 | Sheats |
| 8,130,093 B2 | 3/2012 | Mazar et al. |
| 8,131,351 B2 | 3/2012 | Kalgren et al. |
| 8,131,365 B2 | 3/2012 | Zhang et al. |
| 8,131,565 B2 | 3/2012 | Dicks et al. |
| 8,132,037 B2 | 3/2012 | Fehr et al. |
| 8,135,352 B2 | 3/2012 | Langsweirdt et al. |
| 8,136,735 B2 | 3/2012 | Arai et al. |
| 8,138,925 B2 | 3/2012 | Downie et al. |
| 8,140,160 B2 | 3/2012 | Pless et al. |
| 8,140,168 B2 | 3/2012 | Olson et al. |
| 8,140,299 B2 | 3/2012 | Siess |
| 8,140,312 B2 | 3/2012 | Hayter et al. |
| 8,150,321 B2 | 4/2012 | Winter et al. |
| 8,150,516 B2 | 4/2012 | Levine et al. |
| 8,160,900 B2 | 4/2012 | Taub et al. |
| 8,170,803 B2 | 5/2012 | Kamath et al. |
| 8,179,266 B2 | 5/2012 | Hermle |
| 8,211,016 B2 | 7/2012 | Budiman |
| 8,216,137 B2 | 7/2012 | Budiman |
| 8,216,138 B1 | 7/2012 | McGarraugh et al. |
| 8,224,415 B2 | 7/2012 | Budiman et al. |
| 8,239,166 B2 | 8/2012 | Hayter et al. |
| 8,255,026 B1 | 8/2012 | Al Ali |
| 8,376,945 B2 | 2/2013 | Hayter et al. |
| 8,396,670 B2 | 3/2013 | St-Pierre |
| 8,444,560 B2 | 5/2013 | Hayter et al. |
| 8,457,703 B2 | 6/2013 | Al Ali |
| 8,484,005 B2 | 7/2013 | Hayter et al. |
| 8,532,935 B2 | 9/2013 | Budiman |
| 8,543,354 B2 | 9/2013 | Luo et al. |
| 8,571,808 B2 | 10/2013 | Hayter |
| 8,612,163 B2 | 12/2013 | Hayter et al. |
| 8,657,746 B2 | 2/2014 | Roy |
| 8,682,615 B2 | 3/2014 | Hayter et al. |
| 9,060,719 B2 | 6/2015 | Hayter et al. |
| 9,113,828 B2 | 8/2015 | Budiman |
| 9,241,631 B2 | 1/2016 | Valdes et al. |
| 9,398,872 B2 | 7/2016 | Hayter et al. |
| 9,408,566 B2 | 8/2016 | Hayter et al. |
| 9,483,608 B2 | 11/2016 | Hayter et al. |
| 9,558,325 B2 | 1/2017 | Hayter et al. |
| 10,827,954 B2 | 11/2020 | Hoss et al. |
| 11,000,213 B2 | 5/2021 | Kamath et al. |
| 11,141,084 B2 | 10/2021 | Funderburk et al. |
| 2001/0037366 A1 | 11/2001 | Webb et al. |
| 2001/0041831 A1 | 11/2001 | Starkweather et al. |
| 2002/0010390 A1 | 1/2002 | Guice et al. |
| 2002/0016534 A1 | 2/2002 | Trepagnier et al. |
| 2002/0019022 A1 | 2/2002 | Dunn et al. |
| 2002/0042090 A1 | 4/2002 | Heller et al. |
| 2002/0043651 A1 | 4/2002 | Darrow et al. |
| 2002/0054320 A1 | 5/2002 | Ogino |
| 2002/0065454 A1 | 5/2002 | Lebel et al. |
| 2002/0068860 A1 | 6/2002 | Clark |
| 2002/0072784 A1 | 6/2002 | Sheppard et al. |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0117639 A1 | 8/2002 | Paolini et al. |

(56) References Cited

U.S. PATENT DOCUMENTS

| | | |
|---|---|---|
| 2002/0120186 A1 | 8/2002 | Keimel |
| 2002/0128594 A1 | 9/2002 | Das et al. |
| 2002/0143266 A1 | 10/2002 | Bock |
| 2002/0143372 A1 | 10/2002 | Snell et al. |
| 2002/0147135 A1 | 10/2002 | Schnell |
| 2002/0150959 A1 | 10/2002 | Lejeunne et al. |
| 2002/0156355 A1 | 10/2002 | Gough |
| 2002/0161288 A1 | 10/2002 | Shin et al. |
| 2002/0169635 A1 | 11/2002 | Shillingburg |
| 2002/0177764 A1 | 11/2002 | Sohrab |
| 2002/0193679 A1 | 12/2002 | Malave et al. |
| 2003/0003524 A1 | 1/2003 | Taniike et al. |
| 2003/0004403 A1 | 1/2003 | Drinan et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0028184 A1 | 2/2003 | Lebel et al. |
| 2003/0032077 A1 | 2/2003 | Itoh et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0100040 A1 | 5/2003 | Bonnecaze et al. |
| 2003/0100821 A1 | 5/2003 | Heller et al. |
| 2003/0114897 A1 | 6/2003 | Von Arx et al. |
| 2003/0125612 A1 | 7/2003 | Fox et al. |
| 2003/0130616 A1 | 7/2003 | Steil et al. |
| 2003/0134347 A1 | 7/2003 | Heller et al. |
| 2003/0147515 A1 | 8/2003 | Kai et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0208113 A1 | 11/2003 | Mault et al. |
| 2003/0212317 A1 | 11/2003 | Kovatchev et al. |
| 2003/0212379 A1 | 11/2003 | Bylund et al. |
| 2003/0216630 A1 | 11/2003 | Jersey Willuhn et al. |
| 2003/0217966 A1 | 11/2003 | Tapsak et al. |
| 2003/0235817 A1 | 12/2003 | Bartkowiak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0018486 A1 | 1/2004 | Dunn et al. |
| 2004/0022438 A1 | 2/2004 | Hibbard |
| 2004/0024553 A1 | 2/2004 | Monfre et al. |
| 2004/0039298 A1 | 2/2004 | Abreu |
| 2004/0040840 A1 | 3/2004 | Mao et al. |
| 2004/0041749 A1 | 3/2004 | Dixon |
| 2004/0045879 A1 | 3/2004 | Shults et al. |
| 2004/0054263 A1 | 3/2004 | Moerman et al. |
| 2004/0063435 A1 | 4/2004 | Sakamoto et al. |
| 2004/0064068 A1 | 4/2004 | DeNuzzio et al. |
| 2004/0077962 A1 | 4/2004 | Kroll |
| 2004/0078065 A1 | 4/2004 | Kroll |
| 2004/0093167 A1 | 5/2004 | Braig et al. |
| 2004/0099529 A1 | 5/2004 | Mao et al. |
| 2004/0106858 A1 | 6/2004 | Say et al. |
| 2004/0111017 A1 | 6/2004 | Say et al. |
| 2004/0117204 A1 | 6/2004 | Mazar et al. |
| 2004/0122353 A1 | 6/2004 | Shahmirian et al. |
| 2004/0127777 A1 | 7/2004 | Ruchti et al. |
| 2004/0133164 A1 | 7/2004 | Funderburk et al. |
| 2004/0133390 A1 | 7/2004 | Osorio et al. |
| 2004/0135571 A1 | 7/2004 | Uutela et al. |
| 2004/0135684 A1 | 7/2004 | Steinthal et al. |
| 2004/0138588 A1 | 7/2004 | Saikley et al. |
| 2004/0138716 A1 | 7/2004 | Kon et al. |
| 2004/0142403 A1 | 7/2004 | Hetzel et al. |
| 2004/0146909 A1 | 7/2004 | Duong et al. |
| 2004/0147872 A1 | 7/2004 | Thompson |
| 2004/0152622 A1 | 8/2004 | Keith et al. |
| 2004/0162678 A1 | 8/2004 | Hetzel et al. |
| 2004/0167801 A1 | 8/2004 | Say et al. |
| 2004/0171921 A1 | 9/2004 | Say et al. |
| 2004/0172307 A1 | 9/2004 | Gruber |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193025 A1 | 9/2004 | Steil et al. |
| 2004/0193090 A1 | 9/2004 | Lebel et al. |
| 2004/0197846 A1 | 10/2004 | Hockersmith et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0208780 A1 | 10/2004 | Faries, Jr. et al. |
| 2004/0225338 A1 | 11/2004 | Lebel et al. |
| 2004/0236200 A1 | 11/2004 | Say et al. |
| 2004/0244151 A1 | 12/2004 | Sakata et al. |
| 2004/0249253 A1 | 12/2004 | Racchini et al. |
| 2004/0249420 A1 | 12/2004 | Olson et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0263354 A1 | 12/2004 | Mann et al. |
| 2004/0267300 A1 | 12/2004 | Mace |
| 2005/0001024 A1 | 1/2005 | Kusaka et al. |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0010087 A1 | 1/2005 | Banet et al. |
| 2005/0010269 A1 | 1/2005 | Lebel et al. |
| 2005/0016276 A1 | 1/2005 | Guan et al. |
| 2005/0017864 A1 | 1/2005 | Tsoukalis |
| 2005/0027177 A1 | 2/2005 | Shin et al. |
| 2005/0027180 A1 | 2/2005 | Goode, Jr. et al. |
| 2005/0027181 A1 | 2/2005 | Goode et al. |
| 2005/0027182 A1 | 2/2005 | Siddiqui et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0038332 A1 | 2/2005 | Saidara et al. |
| 2005/0038674 A1 | 2/2005 | Braig et al. |
| 2005/0043598 A1 | 2/2005 | Goode, Jr. et al. |
| 2005/0049179 A1 | 3/2005 | Davidson et al. |
| 2005/0049473 A1 | 3/2005 | Desai et al. |
| 2005/0059871 A1 | 3/2005 | Gough et al. |
| 2005/0070774 A1 | 3/2005 | Addison et al. |
| 2005/0090607 A1 | 4/2005 | Tapsak et al. |
| 2005/0096511 A1 | 5/2005 | Fox et al. |
| 2005/0096512 A1 | 5/2005 | Fox et al. |
| 2005/0096516 A1 | 5/2005 | Soykan et al. |
| 2005/0112169 A1 | 5/2005 | Brauker et al. |
| 2005/0113648 A1 | 5/2005 | Yang et al. |
| 2005/0113653 A1 | 5/2005 | Fox et al. |
| 2005/0113886 A1 | 5/2005 | Fischell et al. |
| 2005/0114068 A1 | 5/2005 | Chey et al. |
| 2005/0115832 A1 | 6/2005 | Simpson et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0134731 A1 | 6/2005 | Lee et al. |
| 2005/0137530 A1 | 6/2005 | Campbell et al. |
| 2005/0143635 A1 | 6/2005 | Kamath et al. |
| 2005/0151976 A1 | 7/2005 | Toma |
| 2005/0154271 A1 | 7/2005 | Rasdal et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0184153 A1 | 8/2005 | Auchinleck |
| 2005/0187442 A1 | 8/2005 | Cho et al. |
| 2005/0187720 A1 | 8/2005 | Goode, Jr. et al. |
| 2005/0192494 A1 | 9/2005 | Ginsberg |
| 2005/0192557 A1 | 9/2005 | Brauker et al. |
| 2005/0195930 A1 | 9/2005 | Spital et al. |
| 2005/0196821 A1 | 9/2005 | Monfre et al. |
| 2005/0197793 A1 | 9/2005 | Baker, Jr. |

(56) References Cited

U.S. PATENT DOCUMENTS

| | | |
|---|---|---|
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0214892 A1 | 9/2005 | Kovatchev et al. |
| 2005/0215871 A1 | 9/2005 | Feldman et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0251033 A1 | 11/2005 | Scarantino et al. |
| 2005/0277164 A1 | 12/2005 | Drucker et al. |
| 2005/0277912 A1 | 12/2005 | John |
| 2005/0283208 A1 | 12/2005 | Von Arx et al. |
| 2005/0287620 A1 | 12/2005 | Heller et al. |
| 2005/0288725 A1 | 12/2005 | Hettrick et al. |
| 2006/0001538 A1 | 1/2006 | Kraft et al. |
| 2006/0001551 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025662 A1 | 2/2006 | Buse et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0058588 A1 | 3/2006 | Zdeblick |
| 2006/0079740 A1 | 4/2006 | Silver et al. |
| 2006/0091006 A1 | 5/2006 | Wang et al. |
| 2006/0094944 A1 | 5/2006 | Chuang |
| 2006/0142651 A1 | 6/2006 | Brister et al. |
| 2006/0154642 A1 | 7/2006 | Scannell |
| 2006/0155180 A1 | 7/2006 | Brister et al. |
| 2006/0166629 A1 | 7/2006 | Reggiardo |
| 2006/0167365 A1 | 7/2006 | Bharmi |
| 2006/0167517 A1 | 7/2006 | Gill et al. |
| 2006/0167518 A1 | 7/2006 | Gill et al. |
| 2006/0167519 A1 | 7/2006 | Gill et al. |
| 2006/0173260 A1 | 8/2006 | Gaoni et al. |
| 2006/0173406 A1 | 8/2006 | Hayes et al. |
| 2006/0173444 A1 | 8/2006 | Choy et al. |
| 2006/0183984 A1 | 8/2006 | Dobbles et al. |
| 2006/0183985 A1 | 8/2006 | Brister et al. |
| 2006/0189851 A1 | 8/2006 | Tvig et al. |
| 2006/0189863 A1 | 8/2006 | Peyser et al. |
| 2006/0193375 A1 | 8/2006 | Lee et al. |
| 2006/0222566 A1 | 10/2006 | Brauker et al. |
| 2006/0224109 A1 | 10/2006 | Steil et al. |
| 2006/0224141 A1 | 10/2006 | Rush et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247685 A1 | 11/2006 | Bharmi |
| 2006/0247710 A1 | 11/2006 | Goetz et al. |
| 2006/0247985 A1 | 11/2006 | Liamos et al. |
| 2006/0253296 A1 | 11/2006 | Liisberg et al. |
| 2006/0258929 A1 | 11/2006 | Goode, Jr. et al. |
| 2006/0258959 A1 | 11/2006 | Sode |
| 2006/0264785 A1 | 11/2006 | Dring et al. |
| 2006/0272652 A1 | 12/2006 | Stocker et al. |
| 2006/0281985 A1 | 12/2006 | Ward et al. |
| 2006/0287691 A1 | 12/2006 | Drew |
| 2006/0290496 A1 | 12/2006 | Peeters et al. |
| 2006/0293576 A1 | 12/2006 | Van Antwerp et al. |
| 2006/0293607 A1 | 12/2006 | Alt et al. |
| 2007/0016381 A1 | 1/2007 | Kamath et al. |
| 2007/0017983 A1 | 1/2007 | Frank et al. |
| 2007/0027381 A1 | 2/2007 | Stafford |
| 2007/0027507 A1 | 2/2007 | Burdett et al. |
| 2007/0032706 A1 | 2/2007 | Kamath et al. |
| 2007/0032717 A1 | 2/2007 | Brister et al. |
| 2007/0033074 A1 | 2/2007 | Nitzan et al. |
| 2007/0038044 A1 | 2/2007 | Dobbles et al. |
| 2007/0038053 A1 | 2/2007 | Berner et al. |
| 2007/0055799 A1 | 3/2007 | Koehler et al. |
| 2007/0056858 A1 | 3/2007 | Chen et al. |
| 2007/0060803 A1 | 3/2007 | Liljeryd et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0066873 A1 | 3/2007 | Kamath et al. |
| 2007/0066956 A1 | 3/2007 | Finkel |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078314 A1 | 4/2007 | Grounsell et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0078818 A1 | 4/2007 | Zvitz et al. |
| 2007/0093786 A1 | 4/2007 | Goldsmith et al. |
| 2007/0095661 A1 | 5/2007 | Wang et al. |
| 2007/0106135 A1 | 5/2007 | Sloan et al. |
| 2007/0108048 A1 | 5/2007 | Wang et al. |
| 2007/0118030 A1 | 5/2007 | Bruce et al. |
| 2007/0118405 A1 | 5/2007 | Campbell et al. |
| 2007/0124002 A1 | 5/2007 | Estes et al. |
| 2007/0129621 A1 | 6/2007 | Kellogg et al. |
| 2007/0149875 A1 | 6/2007 | Ouyang et al. |
| 2007/0156033 A1 | 7/2007 | Causey, III et al. |
| 2007/0163880 A1 | 7/2007 | Woo et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179434 A1 | 8/2007 | Weinert et al. |
| 2007/0191701 A1 | 8/2007 | Feldman et al. |
| 2007/0191702 A1 | 8/2007 | Yodfat et al. |
| 2007/0197889 A1 | 8/2007 | Brauker et al. |
| 2007/0199818 A1 | 8/2007 | Petyt et al. |
| 2007/0202562 A1 | 8/2007 | Curry et al. |
| 2007/0203407 A1 | 8/2007 | Hoss et al. |
| 2007/0203966 A1 | 8/2007 | Brauker et al. |
| 2007/0208244 A1 | 9/2007 | Brauker et al. |
| 2007/0208246 A1 | 9/2007 | Brauker et al. |
| 2007/0213657 A1 | 9/2007 | Jennewine et al. |
| 2007/0227911 A1 | 10/2007 | Wang et al. |
| 2007/0228071 A1 | 10/2007 | Kamen et al. |
| 2007/0232877 A1 | 10/2007 | He |
| 2007/0232878 A1 | 10/2007 | Kovatchev et al. |
| 2007/0232880 A1 | 10/2007 | Siddiqui et al. |
| 2007/0233013 A1 | 10/2007 | Schoenberg et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0253021 A1 | 11/2007 | Mehta et al. |
| 2007/0255116 A1 | 11/2007 | Mehta et al. |
| 2007/0255321 A1 | 11/2007 | Gerber et al. |
| 2007/0255348 A1 | 11/2007 | Holtzclaw |
| 2007/0255531 A1 | 11/2007 | Drew |

(56) References Cited

U.S. PATENT DOCUMENTS

| | | |
|---|---|---|
| 2007/0258395 A1 | 11/2007 | Jollota et al. |
| 2007/0270672 A1 | 11/2007 | Hayter et al. |
| 2007/0282299 A1 | 12/2007 | Hellwig |
| 2007/0285238 A1 | 12/2007 | Batra |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0012701 A1 | 1/2008 | Kass et al. |
| 2008/0017522 A1 | 1/2008 | Heller et al. |
| 2008/0018433 A1 | 1/2008 | Pitt-Pladdy |
| 2008/0021666 A1 | 1/2008 | Goode, Jr. et al. |
| 2008/0021972 A1 | 1/2008 | Huelskamp et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0058773 A1 | 3/2008 | John |
| 2008/0060955 A1 | 3/2008 | Goodnow |
| 2008/0061961 A1 | 3/2008 | John |
| 2008/0064937 A1 | 3/2008 | McGarraugh et al. |
| 2008/0064943 A1 | 3/2008 | Talbot et al. |
| 2008/0066305 A1 | 3/2008 | Wang et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0071580 A1 | 3/2008 | Marcus |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0087544 A1 | 4/2008 | Zhou et al. |
| 2008/0092638 A1 | 4/2008 | Brenneman et al. |
| 2008/0097289 A1 | 4/2008 | Steil et al. |
| 2008/0102441 A1 | 5/2008 | Chen et al. |
| 2008/0108942 A1 | 5/2008 | Brister et al. |
| 2008/0114228 A1 | 5/2008 | McCluskey et al. |
| 2008/0119703 A1 | 5/2008 | Brister et al. |
| 2008/0119705 A1 | 5/2008 | Patel et al. |
| 2008/0119708 A1 | 5/2008 | Budiman |
| 2008/0139910 A1 | 6/2008 | Mastrototaro et al. |
| 2008/0148873 A1 | 6/2008 | Wang |
| 2008/0154513 A1 | 6/2008 | Kovatchev et al. |
| 2008/0161666 A1 | 7/2008 | Feldman et al. |
| 2008/0167543 A1 | 7/2008 | Say et al. |
| 2008/0167572 A1 | 7/2008 | Stivoric et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0183060 A1 | 7/2008 | Steil et al. |
| 2008/0183061 A1 | 7/2008 | Goode et al. |
| 2008/0183399 A1 | 7/2008 | Goode et al. |
| 2008/0188731 A1 | 8/2008 | Brister et al. |
| 2008/0188796 A1 | 8/2008 | Steil et al. |
| 2008/0189051 A1 | 8/2008 | Goode et al. |
| 2008/0194934 A1 | 8/2008 | Ray et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208025 A1 | 8/2008 | Shults et al. |
| 2008/0208113 A1 | 8/2008 | Damiano et al. |
| 2008/0214900 A1 | 9/2008 | Fennell et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0228055 A1 | 9/2008 | Sher |
| 2008/0234943 A1 | 9/2008 | Ray et al. |
| 2008/0234992 A1 | 9/2008 | Ray et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0278331 A1 | 11/2008 | Hayter et al. |
| 2008/0278332 A1 | 11/2008 | Fennel et al. |
| 2008/0287755 A1 | 11/2008 | Sass et al. |
| 2008/0287761 A1 | 11/2008 | Hayter |
| 2008/0287762 A1 | 11/2008 | Hayter |
| 2008/0287763 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0288180 A1 | 11/2008 | Hayter |
| 2008/0288204 A1 | 11/2008 | Hayter et al. |
| 2008/0294024 A1 | 11/2008 | Cosentino et al. |
| 2008/0296155 A1 | 12/2008 | Shults et al. |
| 2008/0300572 A1 | 12/2008 | Rankers et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter et al. |
| 2008/0312844 A1 | 12/2008 | Hayter et al. |
| 2008/0312845 A1 | 12/2008 | Hayter et al. |
| 2008/0314395 A1 | 12/2008 | Kovatchev |
| 2008/0319085 A1 | 12/2008 | Wright et al. |
| 2008/0319279 A1 | 12/2008 | Ramsay et al. |
| 2008/0319295 A1 | 12/2008 | Bernstein et al. |
| 2008/0319296 A1 | 12/2008 | Bernstein et al. |
| 2009/0005665 A1 | 1/2009 | Hayter et al. |
| 2009/0005666 A1 | 1/2009 | Shin et al. |
| 2009/0005729 A1 | 1/2009 | Hendrixson et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0012379 A1 | 1/2009 | Goode et al. |
| 2009/0018424 A1 | 1/2009 | Kamath et al. |
| 2009/0018425 A1 | 1/2009 | Ouyang et al. |
| 2009/0030293 A1 | 1/2009 | Cooper et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036758 A1 | 2/2009 | Brauker et al. |
| 2009/0036760 A1 | 2/2009 | Hayter |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054737 A1 | 2/2009 | Magar et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0054749 A1 | 2/2009 | He |

(56) References Cited

U.S. PATENT DOCUMENTS

| | | |
|---|---|---|
| 2009/0054750 A1 | 2/2009 | Jennewine |
| 2009/0054753 A1 | 2/2009 | Robinson et al. |
| 2009/0055149 A1 | 2/2009 | Hayter et al. |
| 2009/0062633 A1 | 3/2009 | Brauker et al. |
| 2009/0062635 A1 | 3/2009 | Brauker et al. |
| 2009/0062767 A1 | 3/2009 | VanAntwerp et al. |
| 2009/0063187 A1 | 3/2009 | Johnson et al. |
| 2009/0063402 A1 | 3/2009 | Hayter |
| 2009/0069649 A1 | 3/2009 | Budiman |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0093687 A1 | 4/2009 | Telfort et al. |
| 2009/0099436 A1 | 4/2009 | Brister et al. |
| 2009/0102678 A1 | 4/2009 | Mazza et al. |
| 2009/0105554 A1 | 4/2009 | Stahmann et al. |
| 2009/0105560 A1 | 4/2009 | Solomon |
| 2009/0105568 A1 | 4/2009 | Bugler |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0112154 A1 | 4/2009 | Montgomery et al. |
| 2009/0112478 A1 | 4/2009 | Mueller, Jr. et al. |
| 2009/0112626 A1 | 4/2009 | Talbot et al. |
| 2009/0118589 A1 | 5/2009 | Ueshima et al. |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0143725 A1 | 6/2009 | Peyser et al. |
| 2009/0149728 A1 | 6/2009 | Van Antwerp et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0157430 A1 | 6/2009 | Rule et al. |
| 2009/0163789 A1 | 6/2009 | Say et al. |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0182517 A1 | 7/2009 | Gandhi et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0203981 A1 | 8/2009 | Brauker et al. |
| 2009/0204341 A1 | 8/2009 | Brauker et al. |
| 2009/0210249 A1 | 8/2009 | Rasch Menges et al. |
| 2009/0216100 A1 | 8/2009 | Ebner et al. |
| 2009/0216103 A1 | 8/2009 | Brister et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0253973 A1 | 10/2009 | Bashan et al. |
| 2009/0257911 A1 | 10/2009 | Thomas et al. |
| 2009/0267765 A1 | 10/2009 | Greene et al. |
| 2009/0281407 A1 | 11/2009 | Budiman |
| 2009/0287073 A1 | 11/2009 | Boock et al. |
| 2009/0287074 A1 | 11/2009 | Shults et al. |
| 2009/0289796 A1 | 11/2009 | Blumberg |
| 2009/0291634 A1 | 11/2009 | Saarisalo |
| 2009/0294277 A1 | 12/2009 | Thomas et al. |
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2009/0312622 A1 | 12/2009 | Regittnig |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022988 A1 | 1/2010 | Wochner et al. |
| 2010/0023291 A1 | 1/2010 | Hayter et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063372 A1 | 3/2010 | Potts et al. |
| 2010/0063373 A1 | 3/2010 | Kamath et al. |
| 2010/0064764 A1 | 3/2010 | Hayter et al. |
| 2010/0075353 A1 | 3/2010 | Heaton |
| 2010/0076283 A1 | 3/2010 | Simpson et al. |
| 2010/0081906 A1 | 4/2010 | Hayter et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0081953 A1 | 4/2010 | Syeda-Mahmood et al. |
| 2010/0087724 A1 | 4/2010 | Brauker et al. |
| 2010/0093786 A1 | 4/2010 | Watanabe et al. |
| 2010/0094111 A1 | 4/2010 | Heller et al. |
| 2010/0094251 A1 | 4/2010 | Estes et al. |
| 2010/0095229 A1 | 4/2010 | Dixon et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121167 A1 | 5/2010 | McGarraugh et al. |
| 2010/0121169 A1 | 5/2010 | Petisce et al. |
| 2010/0141656 A1 | 6/2010 | Krieftewirth |
| 2010/0152548 A1 | 6/2010 | Koski |
| 2010/0152554 A1 | 6/2010 | Steine et al. |
| 2010/0152561 A1 | 6/2010 | Goodnow et al. |
| 2010/0160757 A1 | 6/2010 | Weinert et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174158 A1 | 7/2010 | Kamath et al. |
| 2010/0174163 A1 | 7/2010 | Brister et al. |
| 2010/0174164 A1 | 7/2010 | Brister et al. |

(56) References Cited

U.S. PATENT DOCUMENTS

| | | |
|---|---|---|
| 2010/0174165 A1 | 7/2010 | Brister et al. |
| 2010/0174166 A1 | 7/2010 | Brister et al. |
| 2010/0174167 A1 | 7/2010 | Kamath et al. |
| 2010/0174168 A1 | 7/2010 | Goode et al. |
| 2010/0174266 A1 | 7/2010 | Estes |
| 2010/0179401 A1 | 7/2010 | Rasdal et al. |
| 2010/0179402 A1 | 7/2010 | Goode et al. |
| 2010/0179404 A1 | 7/2010 | Kamath et al. |
| 2010/0179408 A1 | 7/2010 | Kamath et al. |
| 2010/0179409 A1 | 7/2010 | Kamath et al. |
| 2010/0185065 A1 | 7/2010 | Goode et al. |
| 2010/0185070 A1 | 7/2010 | Brister et al. |
| 2010/0185071 A1 | 7/2010 | Simpson et al. |
| 2010/0185072 A1 | 7/2010 | Goode et al. |
| 2010/0185075 A1 | 7/2010 | Brister et al. |
| 2010/0185175 A1 | 7/2010 | Kamen et al. |
| 2010/0190435 A1 | 7/2010 | Cook et al. |
| 2010/0191082 A1 | 7/2010 | Brister et al. |
| 2010/0191085 A1 | 7/2010 | Budiman |
| 2010/0191087 A1 | 7/2010 | Talbot et al. |
| 2010/0191472 A1 | 7/2010 | Doniger et al. |
| 2010/0198034 A1 | 8/2010 | Thomas et al. |
| 2010/0198035 A1 | 8/2010 | Kamath et al. |
| 2010/0198036 A1 | 8/2010 | Kamath et al. |
| 2010/0198142 A1 | 8/2010 | Sloan et al. |
| 2010/0204557 A1 | 8/2010 | Kiaie et al. |
| 2010/0212583 A1 | 8/2010 | Brister et al. |
| 2010/0213057 A1 | 8/2010 | Feldman et al. |
| 2010/0213080 A1 | 8/2010 | Celentano et al. |
| 2010/0214104 A1 | 8/2010 | Goode et al. |
| 2010/0217557 A1 | 8/2010 | Kamath et al. |
| 2010/0223013 A1 | 9/2010 | Kamath et al. |
| 2010/0223022 A1 | 9/2010 | Kamath et al. |
| 2010/0223023 A1 | 9/2010 | Kamath et al. |
| 2010/0228109 A1 | 9/2010 | Kamath et al. |
| 2010/0228497 A1 | 9/2010 | Kamath et al. |
| 2010/0230285 A1 | 9/2010 | Hoss et al. |
| 2010/0234710 A1 | 9/2010 | Budiman et al. |
| 2010/0240975 A1 | 9/2010 | Goode et al. |
| 2010/0240976 A1 | 9/2010 | Goode et al. |
| 2010/0249530 A1 | 9/2010 | Rankers et al. |
| 2010/0259543 A1 | 10/2010 | Tarassenko et al. |
| 2010/0261987 A1 | 10/2010 | Kamath et al. |
| 2010/0265073 A1 | 10/2010 | Harper et al. |
| 2010/0274107 A1 | 10/2010 | Boock et al. |
| 2010/0274111 A1 | 10/2010 | Say et al. |
| 2010/0274515 A1 | 10/2010 | Hoss et al. |
| 2010/0275108 A1 | 10/2010 | Sloan et al. |
| 2010/0277342 A1 | 11/2010 | Sicurello et al. |
| 2010/0280341 A1 | 11/2010 | Boock et al. |
| 2010/0280441 A1 | 11/2010 | Willinska et al. |
| 2010/0280782 A1 | 11/2010 | Harper et al. |
| 2010/0286496 A1 | 11/2010 | Simpson et al. |
| 2010/0292948 A1 | 11/2010 | Feldman et al. |
| 2010/0298684 A1 | 11/2010 | Leach et al. |
| 2010/0305965 A1 | 12/2010 | Benjamin et al. |
| 2010/0312176 A1 | 12/2010 | Lauer et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0324403 A1 | 12/2010 | Brister et al. |
| 2010/0326842 A1 | 12/2010 | Mazza et al. |
| 2010/0331644 A1 | 12/2010 | Neale et al. |
| 2010/0331648 A1 | 12/2010 | Kamath et al. |
| 2010/0331651 A1 | 12/2010 | Groll |
| 2010/0331656 A1 | 12/2010 | Mensinger et al. |
| 2010/0331657 A1 | 12/2010 | Mensinger et al. |
| 2011/0004085 A1 | 1/2011 | Mensinger et al. |
| 2011/0004276 A1 | 1/2011 | Blair et al. |
| 2011/0009724 A1 | 1/2011 | Hill et al. |
| 2011/0009727 A1 | 1/2011 | Mensinger et al. |
| 2011/0009813 A1 | 1/2011 | Rankers et al. |
| 2011/0010257 A1 | 1/2011 | Hill et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0029247 A1 | 2/2011 | Kalathil |
| 2011/0029269 A1 | 2/2011 | Hayter et al. |
| 2011/0031986 A1 | 2/2011 | Bhat et al. |
| 2011/0036714 A1 | 2/2011 | Zhou et al. |
| 2011/0040163 A1 | 2/2011 | Telson et al. |
| 2011/0046467 A1 | 2/2011 | Simpson et al. |
| 2011/0053121 A1 | 3/2011 | Heaton |
| 2011/0058485 A1 | 3/2011 | Sloan |
| 2011/0060530 A1 | 3/2011 | Fennell |
| 2011/0077469 A1 | 3/2011 | Blocker et al. |
| 2011/0077490 A1 | 3/2011 | Simpson et al. |
| 2011/0077494 A1 | 3/2011 | Doniger et al. |
| 2011/0081726 A1 | 4/2011 | Berman et al. |
| 2011/0082484 A1 | 4/2011 | Saravia et al. |
| 2011/0105873 A1 | 5/2011 | Feldman et al. |
| 2011/0106126 A1 | 5/2011 | Love et al. |
| 2011/0112696 A1 | 5/2011 | Yodfat et al. |
| 2011/0118579 A1 | 5/2011 | Goode et al. |
| 2011/0118580 A1 | 5/2011 | Goode et al. |
| 2011/0123971 A1 | 5/2011 | Berkowitz et al. |
| 2011/0124992 A1 | 5/2011 | Brauker et al. |
| 2011/0124997 A1 | 5/2011 | Goode et al. |
| 2011/0125410 A1 | 5/2011 | Goode et al. |
| 2011/0126188 A1 | 5/2011 | Bernstein et al. |
| 2011/0130970 A1 | 6/2011 | Goode et al. |
| 2011/0130971 A1 | 6/2011 | Goode et al. |
| 2011/0130998 A1 | 6/2011 | Goode et al. |
| 2011/0137571 A1 | 6/2011 | Power et al. |
| 2011/0144465 A1 | 6/2011 | Shults et al. |
| 2011/0148905 A1 | 6/2011 | Simmons et al. |
| 2011/0152637 A1 | 6/2011 | Kateraas et al. |
| 2011/0163880 A1 | 7/2011 | Halff et al. |
| 2011/0163881 A1 | 7/2011 | Halff et al. |
| 2011/0178378 A1 | 7/2011 | Brister et al. |
| 2011/0184268 A1 | 7/2011 | Taub |
| 2011/0184752 A1 | 7/2011 | Ray et al. |
| 2011/0190603 A1 | 8/2011 | Stafford |
| 2011/0190614 A1 | 8/2011 | Brister et al. |
| 2011/0191044 A1 | 8/2011 | Stafford |
| 2011/0193704 A1 | 8/2011 | Harper et al. |
| 2011/0196217 A1 | 8/2011 | Myoujou et al. |
| 2011/0201910 A1 | 8/2011 | Rasdal et al. |
| 2011/0201911 A1 | 8/2011 | Johnson et al. |
| 2011/0208027 A1 | 8/2011 | Wagner et al. |
| 2011/0208155 A1 | 8/2011 | Palerm et al. |
| 2011/0210830 A1 | 9/2011 | Talty et al. |
| 2011/0213225 A1 | 9/2011 | Bernstein et al. |
| 2011/0218414 A1 | 9/2011 | Kamath et al. |
| 2011/0224523 A1 | 9/2011 | Budiman |
| 2011/0231107 A1 | 9/2011 | Brauker et al. |
| 2011/0231140 A1 | 9/2011 | Goode et al. |
| 2011/0231141 A1 | 9/2011 | Goode et al. |
| 2011/0231142 A1 | 9/2011 | Goode et al. |
| 2011/0253533 A1 | 10/2011 | Shults et al. |
| 2011/0257495 A1 | 10/2011 | Hoss et al. |
| 2011/0257895 A1 | 10/2011 | Brauker et al. |
| 2011/0263958 A1 | 10/2011 | Brauker et al. |
| 2011/0263959 A1 | 10/2011 | Young et al. |
| 2011/0264378 A1 | 10/2011 | Breton et al. |
| 2011/0270062 A1 | 11/2011 | Goode et al. |
| 2011/0270158 A1 | 11/2011 | Brauker et al. |
| 2011/0275919 A1 | 11/2011 | Petisce et al. |
| 2011/0282327 A1 | 11/2011 | Kellogg et al. |
| 2011/0287528 A1 | 11/2011 | Fern et al. |
| 2011/0288574 A1 | 11/2011 | Curry et al. |
| 2011/0289497 A1 | 11/2011 | Kiaie et al. |
| 2011/0290645 A1 | 12/2011 | Brister et al. |
| 2011/0313543 A1 | 12/2011 | Brauker et al. |
| 2011/0319729 A1 | 12/2011 | Donnay et al. |
| 2011/0319739 A1 | 12/2011 | Kamath et al. |
| 2011/0320130 A1 | 12/2011 | Valdes et al. |
| 2011/0320167 A1 | 12/2011 | Budiman |
| 2012/0010642 A1 | 1/2012 | Lee et al. |

(56) References Cited

U.S. PATENT DOCUMENTS

| | | |
|---|---|---|
| 2012/0035445 A1 | 2/2012 | Boock et al. |
| 2012/0040101 A1 | 2/2012 | Tapsak et al. |
| 2012/0046534 A1 | 2/2012 | Simpson et al. |
| 2012/0078071 A1 | 3/2012 | Bohm et al. |
| 2012/0084053 A1 | 4/2012 | Yuen et al. |
| 2012/0108931 A1 | 5/2012 | Taub |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0186997 A1 | 7/2012 | Li et al. |
| 2012/0209099 A1 | 8/2012 | Ljuhs et al. |
| 2012/0215462 A1 | 8/2012 | Goode et al. |
| 2012/0233679 A1 | 9/2012 | Shedrinsky |
| 2012/0238851 A1 | 9/2012 | Kamen et al. |
| 2012/0245447 A1 | 9/2012 | Karan et al. |
| 2012/0255875 A1 | 10/2012 | Vicente et al. |
| 2012/0277565 A1 | 11/2012 | Budiman |
| 2012/0283542 A1 | 11/2012 | McGarraugh |
| 2012/0309302 A1 | 12/2012 | Buhot |
| 2012/0318670 A1 | 12/2012 | Karinka et al. |
| 2013/0035575 A1 | 2/2013 | Mayou et al. |
| 2013/0137953 A1 | 5/2013 | Harper et al. |
| 2013/0184547 A1 | 7/2013 | Taub et al. |
| 2013/0225959 A1 | 8/2013 | Bugler |
| 2013/0231541 A1 | 9/2013 | Hayter et al. |
| 2013/0235166 A1 | 9/2013 | Jones et al. |
| 2013/0245547 A1 | 9/2013 | El Khatib et al. |
| 2013/0324823 A1 | 12/2013 | Koski et al. |
| 2014/0005499 A1 | 1/2014 | Catt et al. |
| 2014/0046160 A1 | 2/2014 | Terashima et al. |
| 2014/0088392 A1 | 3/2014 | Bernstein et al. |
| 2014/0121480 A1 | 5/2014 | Budiman et al. |
| 2014/0121488 A1 | 5/2014 | Budiman |
| 2014/0221966 A1 | 8/2014 | Buckingham et al. |
| 2014/0275898 A1 | 9/2014 | Taub et al. |
| 2015/0005601 A1 | 1/2015 | Hoss et al. |
| 2015/0216456 A1 | 8/2015 | Budiman |
| 2015/0241407 A1 | 8/2015 | Ou et al. |
| 2015/0366510 A1 | 12/2015 | Budiman |
| 2016/0022221 A1 | 1/2016 | Ou et al. |
| 2016/0245791 A1 | 8/2016 | Hayter et al. |
| 2016/0302701 A1 | 10/2016 | Bhavaraju et al. |
| 2016/0317069 A1 | 11/2016 | Hayter et al. |
| 2017/0053084 A1 | 2/2017 | McMahon et al. |
| 2017/0086756 A1 | 3/2017 | Harper et al. |
| 2017/0185748 A1 | 6/2017 | Budiman et al. |

FOREIGN PATENT DOCUMENTS

| | | |
|---|---|---|
| CA | 2626349 | 9/2008 |
| CA | 2728831 | 7/2011 |
| CA | 2617965 | 10/2011 |
| DE | 4401400 | 7/1995 |
| EP | 0098592 | 1/1984 |
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0472411 | 2/1992 |
| EP | 0286118 | 1/1995 |
| EP | 0867146 | 9/1998 |
| EP | 1048264 | 11/2000 |
| EP | 1 391 728 | 2/2004 |
| EP | 1419731 | 5/2004 |
| EP | 0939602 | 9/2004 |
| EP | 1725163 | 11/2006 |
| EP | 2031534 | 3/2009 |
| EP | 1850909 | 4/2010 |
| EP | 1677668 | 7/2010 |
| EP | 1 413 879 | 1/2012 |
| EP | 2 498 196 | 9/2012 |
| EP | 3 575 796 | 12/2019 |
| WO | WO 1996/025089 | 8/1996 |
| WO | WO 1996/035370 | 11/1996 |
| WO | WO 97/18639 | 5/1997 |
| WO | WO 1997/015227 | 5/1997 |
| WO | WO 1998/035053 | 8/1998 |
| WO | WO 1999/027849 | 6/1999 |
| WO | WO 1999/028736 | 6/1999 |
| WO | WO 1999/056613 | 11/1999 |
| WO | WO 00/49941 | 8/2000 |
| WO | WO 2000/049940 | 8/2000 |
| WO | WO 2000/059370 | 10/2000 |
| WO | WO 2000/074753 | 12/2000 |
| WO | WO 2000/078992 | 12/2000 |
| WO | WO 2001/052935 | 7/2001 |
| WO | WO 2001/054753 | 8/2001 |
| WO | WO 2002/016905 | 2/2002 |
| WO | WO 02/058537 | 8/2002 |
| WO | WO 2002/058537 | 8/2002 |
| WO | WO 03/012422 | 2/2003 |
| WO | WO 03/032411 | 4/2003 |
| WO | WO 2003/057027 | 7/2003 |
| WO | WO 2003/076893 | 9/2003 |
| WO | WO 2003/082091 | 10/2003 |
| WO | WO 2003/085372 | 10/2003 |
| WO | WO 03/094714 | 11/2003 |
| WO | WO 2004/060455 | 7/2004 |
| WO | WO 2004/061420 | 7/2004 |
| WO | WO 2005/010756 | 2/2005 |
| WO | WO 2005/011489 | 2/2005 |
| WO | WO 2005/057175 | 6/2005 |
| WO | WO 2005/065538 | 7/2005 |
| WO | WO 2005/065542 | 7/2005 |
| WO | WO 2005/070287 | 8/2005 |
| WO | WO 2005/089103 | 9/2005 |
| WO | WO 2006/020212 | 2/2006 |
| WO | WO 2006/024671 | 3/2006 |
| WO | WO 2006/072035 | 7/2006 |
| WO | WO 2006/079114 | 7/2006 |
| WO | WO 2006/081336 | 8/2006 |
| WO | WO 2006/085087 | 8/2006 |
| WO | WO 2006/086423 | 8/2006 |
| WO | WO 2007/019289 | 2/2007 |
| WO | WO 2007/097754 | 8/2007 |
| WO | WO 2008/001366 | 1/2008 |
| WO | WO 2008/021913 | 2/2008 |
| WO | WO 2008/048452 | 4/2008 |
| WO | WO 2008/052374 | 5/2008 |
| WO | WO 2008/062099 | 5/2008 |
| WO | WO 2008/086541 | 7/2008 |
| WO | WO 2008/144445 | 11/2008 |
| WO | WO 2009/097594 | 8/2009 |
| WO | WO 2010/022387 | 2/2010 |
| WO | WO 2010/062898 | 6/2010 |
| WO | WO 2010/099507 | 9/2010 |
| WO | WO 2011/000528 | 1/2011 |
| WO | WO 2011/011643 | 1/2011 |
| WO | WO 2011/104616 | 9/2011 |
| WO | WO 2012/142502 | 10/2012 |
| WO | WO 2013/019225 | 2/2013 |

OTHER PUBLICATIONS

U.S. Appl. No. 16/902,111 (US 2020/0305803), Aug. 14, 2020 Response to Non Final Office Action.

U.S. Appl. No. 16/902,111 (US 2020/0305803), Jul. 6, 2020 Non Final Office Action.

Alemzadeh, R, "Sensor Augmented Insulin Pump Therapy: Clinical Applications", Medical College of Wisconsin Diabetes Symposium, pp. 1 61, 2011.

Armour, J. C., et al., "Application of Chronic Intravascular Blood Glucose Sensor in Dogs", Diabetes, vol. 39, 1990, pp. 1519 1526.

Arnold, M. A., et al., "Selectivity Assessment of Noninvasive Glucose Measurements Based on Analysis of Multivariate Calibration Vectors", Journal of Diabetes Science and Technology, vol. 1, No. 4, 2007, pp. 454 462.

Bennion, N., et al., "Alternate Site Glucose Testing: A Crossover Design", Diabetes Technology & Therapeutics, vol. 4, No. 1, 2002, pp. 25 33.

(56) References Cited

OTHER PUBLICATIONS

Blank, T. B., et al., "Clinical Results from a Non Invasive Blood Glucose Monitor", Optical Diagnostics and Sensing of Biological Fluids and Glucose and Cholesterol Monitoring II, Proceedings of SPIE, vol. 4624, 2002, pp. 1 10.

Blendea, M. C., et al., "Heart Disease in Diabetic Patients", Current Diabetes Reports, vol. 3, 2003, pp. 223 229.

Boyne, M. S., et al., "Timing of Changes in Interstitial and Venous Blood Glucose Measured with a Continuous Subcutaneous Glucose Sensor", Diabetes, vol. 52, Nov. 2003, pp. 2790 2794.

Bremer, T. M., et al., "Benchmark Data from the Literature for Evaluation of New Glucose Sensing Technologies", Diabetes Technology & Therapeutics, vol. 3, No. 3, 2001, pp. 409 418.

Brooks, S. L., et al., "Development of an On-Line Glucose Sensor for Fermentation Monitoring", Biosensors, vol. 3, 1987/88, pp. 45 56.

Cass, A. E., et al., "Ferrocene Medicated Enzyme Electrode for Amperometric Determination of Glucose", Analytical Chemistry, vol. 56, No. 4, 1984, 667 671.

Cheyne, E. H., et al., "Performance of a Continuous Glucose Monitoring System During Controlled Hypoglycaemia in Healthy Volunteers", Diabetes Technology & Therapeutics, vol. 4, No. 5, 2002, pp. 607 613.

Choleau, C., et al., "Calibration of a Subcutaneous Amperometric Glucose Sensor Implanted for 7 Days in Diabetic Patients Part 2. Superiority of the One Point Calibration Method", Biosensors and Bioelectronics, vol. 17, No. 8, 2002, pp. 647 654.

Csoregi, E., et al., "Design and Optimization of a Selective Subcutaneously Implantable Glucose Electrode Based on 'Wired' Glucose Oxidase", Analytical Chemistry, vol. 67, No. 7, 1995, pp. 1240 1244.

Diabetes Control and Complications Trial Research Group, "The Effect of Intensive Treatment of Diabetes on the Development and Progression of Long Term Complications in Insulin Dependent Diabetes Mellitus," New England J. Med. vol. 329, 1993, pp. 977 986.

Eckert, B. et al. "Hypoglycaemia Leads to an Increased QT Interval in Normal Men," Clinical Physiology, vol. 18, No. 6, 1998, pp. 570 575.

El Khatib, F. H, et al., "Adaptive Closed Loop Control Provides Blood Glucose Regulation Using Subcutaneous Insulin and Glucagon Infusion in Diabetic Swine", Journal of Diabetes Science and Technology, vol. 1, No. 2, 2007, pp. 181 192.

Eren Oruklu, M., et al., "Estimation of Future Glucose Concentrations with Subject Specific Recursive Linear Models", Diabetes Technology & Therapeutics vol. 11(4), 2009, pp. 243 253.

Feldman, B., et al., "A Continuous Glucose Sensor Based on Wired EnzymeTM Technology Results from a 3 Day Trial in Patients with Type 1 Diabetes", Diabetes Technology & Therapeutics, vol. 5, No. 5, 2003, pp. 769 779.

Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.

Georgescu, B., et al., "Real Time Multimodel Tracking of Myocardium in Echocardiography Using Robust Information Fusion", Medical Image Computing and Computer Assisted Intervention, 2004, pp. 777 785.

Goldman, J. M., et al., "Masimo Signal Extraction Pulse Oximetly", Journal of Clinical Monitoring and Computing, vol. 16, No. 7, 2000, pp. 475 483.

Guerci, B., et al., "Clinical Performance of CGMS in Type 1 Diabetic Patients Treated by Continuous Subcutaneous Insulin Infusion Using Insulin Analogs", Diabetes Care, vol. 26, 2003, pp. 582 589.

Harris, N.D., et al., "Can Changes in QT Interval be Used to Predict the Onset of Hypoglycemia in Type 1 Diabetes?", Computers in Cardiology, vol. 27, 2000, pp. 375 378.

Heller, S. R., "Abnormalities of the Electrocardiogram During Hypoglycemia: The Cause of the Dead in Bed Syndrome?" International Journal of Clinical Practice, Suppl. No. 129, 2002, pp. 27 32.

Hovorka, R., et al., "Nonlinear Model Predictive Control of Glucose Concentration in Subjects with Type 1 Diabetes", Physiological Measurement, vol. 55, Jul. 2004, pp. 905 920.

Isermann, R., "Supervision, Fault Detection and Fault Diagnosis Methods—An Introduction", Control Engineering Practice, vol. 5, No. 5, 1997, pp. 639 652.

Isermann, R., et al., "Trends in the Application of Model Based Fault Detection and Diagnosis of Technical Processes", Control Engineering Practice, vol. 5, No. 5, 1997, pp. 709 719.

Johnson, P. C., "Peripheral Circulation", John Wiley & Sons, 1978, pp. 198.

Jones, T. W., et al., "Mild Hypoglycemia and Impairment of Brain Stem and Cortical Evoked Potentials in Healthy Subjects," Diabetes vol. 39, 1990, 1550 1555.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", Diabetes Care, vol. 24, No. 7, 2001, pp. 1303 1304.

Kaplan, S. M., "Wiley Electrical and Electronics Engineering Dictionary", IEEE Press, 2004, pp. 141, 142, 548, 549.

Kovatchev, B. P., et al., "Evaluating the Accuracy of Continuous Glucose Monitoring Sensors", Diabetes Care, vol. 27, No. 8, 2004, pp. 1922 1928.

Kovatchev, B. P., et al., "Graphical and Numerical Evaluation of Continuous Glucose Sensing Time Lag", Diabetes Technology & Therapeutics, vol. 11, No. 3, Feb. 2009, pp. 139 143.

Kuure Kinsey, M., et al., "A Dual Rate Kalman Filter for Continuous Glucose Monitoring", Proceedings of the 28th IEEE, EMBS Annual International Conference, New York City, 2006, pp. 63 66.

Landstedt Hallin, L., et al., "Increased QT Dispersion During Hypoglycaemia in Patients with Type 2 Diabetes Mellitus," Journal of Internal Medicine, vol. 246, 1999, 299 307.

Lodwig, V., et al., "Continuous Glucose Monitoring with Glucose Sensors: Calibration and Assessment Criteria", Diabetes Technology & Therapeutics, vol. 5, No. 4, 2003, pp. 573 587.

Lortz, J., et al., "What is Bluetooth? We Explain The Newest Short Range Connectivity Technology", Smart Computing Learning Series, Wireless Computing, vol. 8, Issue 5, 2002, pp. 72 74.

Maher, "A Method for Extrapolation of Missing Digital Audio Data", Preprints of Papers Presented at the AES Convention, 1993, pp. 1 19.

Maher, "Audio Enhancement using Nonlinear Time Frequency Filtering", AES $26^{th}$ International Conference, 2005, pp. 1 9.

Malin, S. F., et al., "Noninvasive Prediction of Glucose by Near Infrared Diffuse Reflectance Spectoscopy", Clinical Chemistry, vol. 45, No. 9, 1999, pp. 1651 1658.

Malmberg, K., "Prospective Randomised Study of Intensive Insulin Treatment on Long Term Survival After Acute Myocardial Infarction in Patients with Diabetes Mellitus", British Medical Journal, vol. 314, 1997, pp. 1512 1515.

Markel, A. et al., "Hypoglycaemia Induced Ischaemic ECG Changes", Presse Medicale, vol. 23, No. 2, 1994, pp. 78 79.

McGarraugh, G., et al., "Glucose Measurements Using Blood Extracted from the Forearm and the Finger", TheraSense, Inc., 2001, 16 Pages.

McGarraugh, G., et al., "Physiological Influences on Off Finger Glucose Testing", Diabetes Technology & Therapeutics, vol. 3, No. 3, 2001, pp. 367 376.

McKean, B. D., et al., "A Telemetry Instrumentation System for Chronically Implanted Glucose and Oxygen Sensors", IEEE Transactions on Biomedical Engineering, vol. 35, No. 7, 1988, pp. 526 532.

Morbiducci, U, et al., "Improved Usability of the Minimal Model of Insulin Sensitivity Based on an Automated Approach and Genetic Algorithms for Parameter Estimation", Clinical Science, vol. 112 2007, pp. 257 263.

(56) References Cited

OTHER PUBLICATIONS

Mougiakakou, et al., "A Real Time Simulation Model of Glucose Insulin Metabolism for Type 1 Diabetes Patients", Proceedings of the 2005 IEEE, 2005, pp. 298 301.
Okin, P. M., et al., "Electrocardiographic Repolarization Complexity and Abnormality Predict All Cause and Cardiovascular Mortality in Diabetes," Diabetes, vol. 53, 2004, pp. 434 440.
Panteleon, A. E., et al., "The Role of the Independent Variable to Glucose Sensor Calibration", Diabetes Technology & Therapeutics, vol. 5, No. 3, 2003, pp. 401 410.
Parker, R., et al., "Robust Hoe Glucose Control in Diabetes Using a Physiological Model", AIChE Journal, vol. 46, No. 12, 2000, pp. 2537 2549.
Person, K., et al., Regulation of Serum Potassium During Insulin Induced Hypoglycemia, Diabetes, vol. 31, 1982, pp. 615 617.
Pickup, J., et al., "Implantable Glucose Sensors: Choosing the Appropriate Sensing Strategy", Biosensors, vol. 3, 1987/88, pp. 335 346.
Pickup, J., et al., "In Vivo Molecular Sensing in Diabetes Mellitus: An Implantable Glucose Sensor with Direct Electron Transfer", Diabetologia, vol. 32, 1989, pp. 213 217.
Pishko, M. V., et al., "Amperometric Glucose Microelectrodes Prepared Through Immobilization of Glucose Oxidase in Redox Hydrogels", Analytical Chemistry, vol. 63, No. 20, 1991, pp. 2268 2272.
Quinn, C. P., et al., "Kinetics of Glucose Delivery to Subcutaneous Tissue in Rats Measured with 0.3 mm Amperometric Microsensors", The American Physiological Society, 1995, E155 E161.
Rana, B. S., et al., "Relation of QT Interval Dispersion to the Number of Different Cardiac Abnormalities in Diabetes Mellitus", The American Journal of Cardiology, vol. 90, 2002, pp. 483 487.
Robinson, R. T. C. E., et al. "Changes in Cardiac Repolarization During Clinical Episodes of Nocturnal Hypoglycaemia in Adults with Type 1 Diabetes," Diabetologia, vol. 47, 2004, pp. 312 315.
Roe, J. N., et al., "Bloodless Glucose Measurements", Critical Review in Therapeutic Drug Carrier Systems, vol. 15, Issue 3, 1998, pp. 199 241.
Sakakida, M., et al., "Development of Ferrocene Mediated Needle Type Glucose Sensor as a Measure of True Subcutaneous Tissue Glucose Concentrations", Artificial Organs Today, vol. 2, No. 2, 1992, pp. 145 158.
Sakakida, M., et al., "Ferrocene Mediated Needle Type Glucose Sensor Covered with Newly Designed Biocompatible Membrane", Sensors and Actuators B, vol. 13 14, 1993, pp. 319 322.
Salehi, C., et al., "A Telemetry Instrumentation System for Long Term Implantable Glucose and Oxygen Sensors", Analytical Letters, vol. 29, No. 13, 1996, pp. 2289 2308.
Schmidtke, D. W., et al., "Measurement and Modeling of the Transient Difference Between Blood and Subcutaneous Glucose Concentrations in the Rat After Injection of Insulin", Proceedings of the National Academy of Sciences, vol. 95, 1998, pp. 294 299.
Shaw, G. W., et al., "In Vitro Testing of a Simply Constructed, Highly Stable Glucose Sensor Suitable for Implantation in Diabetic Patients", Biosensors & Bioelectronics, vol. 6, 1991, pp. 401 406.
Shichiri, M., et al., "Glycaemic Control in Pancreatectomized Dogs with a Wearable Artificial Endocrine Pancreas", Diabetologia, vol. 24, 1983, pp. 179 184.
Shichiri, M., et al., "In Vivo Characteristics of Needle Type Glucose Sensor Measurements of Subcutaneous Glucose Concentrations in Human Volunteers", Hormone and Metabolic Research Supplement Series, vol. 20, 1988, pp. 17 20.
Shichiri, M., et al., "Membrane Design for Extending the Long Life of an Implantable Glucose Sensor", Diabetes Nutrition and Metabolism, vol. 2, 1989, pp. 309 313.
Shichiri, M., et al., "Needle type Glucose Sensor for Wearable Artificial Endocrine Pancreas", Implantable Sensors for Closed Loop Prosthetic Systems, Chapter 15, 1985, pp. 197 210.

Shichiri, M., et al., "Telemetry Glucose Monitoring Device with Needle Type Glucose Sensor: A Useful Tool for Blood Glucose Monitoring in Diabetic Individuals", Diabetes Care, vol. 9, No. 3, 1986, pp. 298 301.
Shichiri, M., et al., "Wearable Artificial Endocrine Pancreas with Needle Type Glucose Sensor", The Lancet, 1982, pp. 1129 1131.
Shults, M. C., et al., "A Telemetry Instrumentation System for Monitoring Multiple Subcutaneously Implanted Glucose Sensors", IEEE Transactions on Biomedical Engineering, vol. 41, No. 10, 1994, pp. 937 942.
Steil, G. M., et al., "Closed Loop Insulin Delivery the Path of Physiological Glucose Control", Advanced Drug Delivery Reviews, vol. 56, 2004, pp. 125 144.
Steil, G. M., et al., "Determination of Plasma Glucose During Rapid Glucose Excursions with a Subcutaneous Glucose Sensor", Diabetes Technology & Therapeutics, vol. 5, No. 1, 2003, pp. 27 31.
Steinhaus, B. M., et al., "The Information Content of the Cardiac Electrogram at the Stimulus Site," Annual International Conference of the IEEE Engineering in Medicine and Biology Society, vol. 12, No. 2, 1990, 0607 0609.
Sternberg, R., et al., "Study and Development of Multilayer Needle Type Enzyme Based Glucose Microsensors", Biosensors, vol. 4, 1988, pp. 27 40.
Thompson, M., et al., "In Vivo Probes: Problems and Perspectives", Clinical Biochemistry, vol. 19, 1986, pp. 255 261.
Turner, A., et al., "Diabetes Mellitus: Biosensors for Research and Management", Biosensors, vol. 1, 1985, pp. 85 115.
Updike, S. J., et al., "Principles of Long Term Fully Implanted Sensors with Emphasis on Radiotelemetric Monitoring of Blood Glucose from Inside a Subcutaneous Foreign Body Capsule (FBC)", Biosensors in the Body: Continuous in vivo Monitoring, Chapter 4, 1997, pp. 117 137.
Velho, G., et al., "Strategies for Calibrating a Subcutaneous Glucose Sensor", Biomedica Biochimica Acta, vol. 48, 1989, pp. 957 964.
Whipple, G., "Low Residual Noise Speech Enhancement Utilizing Time Frequency", Proceedings of the International Conference on Acoustics, Speech, and Signal Processing, vol. 19, 1994, pp. I/5-I/8.
Wilson, G. S., et al., "Progress Toward the Development of an Implantable Sensor for Glucose", Clinical Chemistry, vol. 38, No. 9, 1992, pp. 1613 1617.
Wolfe, P. J., et al., "Interpolation of Missing Data Values for Audio Signal Restoration Using a Gabor Regression Model", 2005 IEEE International Conference on Acoustics, Speech, and Signal Processing, vol. 5, 2005, pp. 517 520.
European Patent Application No. 10812728.3, Examination Report dated Feb. 28, 2018.
European Patent Application No. 13841355.4, Extended European Search Report dated Apr. 1, 2016.
European Patent Application No. 10812728.3, Extended European Search Report dated Aug. 21, 2014.
Israeli Patent Application No. 216631, Original Language and English Translation of Official Action dated Sep. 18, 2014.
PCT Application No. PCT/US2013/060471, International Preliminary Report on Patentability and Written Opinion of the International Searching Authority dated Apr. 9, 2015.
PCT Application No. PCT/US2013/060471, International Search Report and Written Opinion of the International Searching Authority dated Feb. 10, 2014.
PCT Application No. PCT/US2010/047194, International Preliminary Report on Patentability and Written Opinion of the International Searching Authority dated Mar. 15, 2012.
PCT Application No. PCT/US2010/047194, International Search Report and Written Opinion of the International Searching Authority dated Dec. 29, 2010.
U.S. Appl. No. 12/871,901, Notice of Allowance dated Apr. 17, 2013.
U.S. Appl. No. 12/871,901, Office Action dated Oct. 25, 2012.
U.S. Appl. No. 13/970,556, Notice of Allowance dated Mar. 20, 2014.
U.S. Appl. No. 13/970,556, Office Action dated Nov. 5, 2013.
U.S. Appl. No. 14/431,168, Notice of Allowance dated Dec. 21, 2017.
U.S. Appl. No. 14/457,066, Notice of Allowance dated Sep. 9, 2015.

(56) References Cited

OTHER PUBLICATIONS

U.S. Appl. No. 14/457,066, Office Action dated Jul. 7, 2015.
U.S. Appl. No. 14/592,704, Notice of Allowance dated Oct. 28, 2015.
U.S. Appl. No. 14/592,704, Office Action dated Sep. 17, 2015.
U.S. Appl. No. 14/938,840, Notice of Allowance dated Oct. 27, 2016.
U.S. Appl. No. 14/938,840, Office Action dated May 12, 2016.
U.S. Appl. No. 15/199,765, Office Action dated Apr. 5, 2018.
U.S. Appl. No. 15/260,288, Office Action dated Jun. 27, 2017.
U.S. Appl. No. 15/377,989, Notice of Allowance dated Jul. 18, 2017.
U.S. Appl. No. 15/808,918, Notice of Allowance dated Jul. 19, 2018.
U.S. Appl. No. 16/181,081, Notice of Allowance dated Jun. 21, 2019.
U.S. Appl. No. 16/664,083, Notice of Allowance dated Aug. 11, 2020.
Abel, et al., "Biosensors for in vivo glucose measurement: can we cross the experimental stage", Biosensors and Bioelectronics, 17:1059-1070 (2002).
Alcock, et al., "Continuous Analyte Monitoring to Aid Clinical Practice", IEEE Engineering in Medicine and Biology, pp. 319-325 (1994).
Bard, et al., Electrochemical Methods, Fundamentals and Applications, pp. 174-175 (1980).
Bequette, "Continuous Glucose Monitoring: Real Time Algorithms for Calibration, Filtering, and Alarms", Journal of Diabetes Science and Technology, 4(2):404-418 (2010).
"Blood glucose monitoring" retrieved from "https://web.archive.org/web/20111215063153/http://en.wikipedia.org/wiki/Blood_glucose_monitoring" on Aug. 1, 2021, 6 pages.
Cengiz, et al., "A Tale of Two Compartments: Interstitial Versus Blood Glucose Monitoring", Diabetes Technology & Therapeutics, 11(1):S-11-S16 (2009).
Chen, et al., "Glucose microbiosensor based on alumina sol gel matrix/eletropolymerized composite membrane", Biosensors and Bioelectronics, 17:1005-1013 (2002).
Chen, et al., "Defining the Period of Recovery of the Glucose Concentration after Its Local Perturbation by the Implantation of a Miniature Sensor", Clin Chem Lab Med, 40(8):786-789 (2002).
Chen, et al., "In Situ Assembled Mass-Transport Controlling Micromembranes and Their Application in Implanted Amperometric Glucose Sensors", Analytical Chemistry, 72(16):3757-3763 (2000).
Chen, et al., "In vivo Glucose Monitoring with Miniature "Wired" Glucose Oxidase Electrodes", Analytical Sciences, 17:i297-i300 (2001).
Choleau et al., "Calibration of a subcutaneous amperometric glucose sensor—Part 1. Effect of measurement uncertainties on the determination of sensor sensitivity and background current," Biosensors and Bioelectronics 17, 641-646 (2002).
Chung, "In vitro Evaluation of the Continuous Monitoring Glucose Sensors with Perfluorinated Tetrafluoroethylene Coatings", Bull. Korean Chem. Soc., 24(4):514-516 (2003).
Csöregi et al., "Design, Characterization, and One-Point in Vivo Calibration of a Subcutaneously Implanted Glucose Electrode," Anal. Chem., 66, 3131-3138 (1994).
De Block, et al., "Minimally-Invasive and Non-Invasive Continuous Glucose Monitoring Systems: Indications, Advantages, Limitations and Clinical Aspects", Current Diabetes Reviews, 4:159-168 (2008).
Decuir, "Bluetooth 4.0:Low Energy", Standards Architect, CSR Technology, Councilor, Bluetooth Architecture Review Board, IEEE Region 6 Northwest Area Chair, 104 pages (2012).
Dementyev, et al., "Power Consumption Analysis of Bluetooth Low Energy, ZigBee and ANT Sensor Nodes in a Cyclic Sleep Scenario", IEEE International Wireless Symposium (IWS), 5 pages (2013).
Facchinetti, et al., "Enhanced Accuracy of Continuous Glucose Monitoring by Online Extended Kalman Filtering", Diabetes Technology & Therapeutics, 12(5):353-363 (2010).
Feldman, et al., "A Continuous Glucose Sensor Based on Wired Enzyme™ Technology—Results from a 3-Day Trial in Patients with Type 1 Diabetes", Diabetes Technology & Therapeutics, 5(5):769-779 (2003).
Fisher, "Fundamentals of Glucose Sensors," Diabetic Medicine, 8: 309-321 (1991).
Fraser, "An Introduction to in vivo Biosensing: Progress and Problems", Biosensors in the Body: Continuous in vivo Monitoring, pp. 1-56 (1997).
Frost, et al., "Implantable chemical sensors for real-time clinical monitoring: progress and challenges", Current Opinion in Chemical Biology, 6:633-641 (2002).
Gerritsen, et al., "Subcutaneously implantable glucose sensors in patients with diabetes mellitus; still many problems", Dutch Journal of Medicine, 146(28):1313-1316 (2002) (with English Machine Translation).
Heinemann, "Continuous Glucose Monitoring by Means of the Microdialysis Technique: Underlying Fundamental Aspects", Diabetes Technology & Therapeutics, 5(4):545-561 (2003).
Heise, et al., "Hypoglycemia Warning Signal and Glucose Sensors: Requirements and Concepts", Diabetes Technology & Therapeutics, 5(4):563-571 (2003).
Heller, "Implanted Electrochemical Glucose Sensors for the Management of Diabetes", Annu. Rev. Biomed. Eng., 01:153-175 (1999).
"In Vivo Glucose Sensing", Chemical Analysis, A Series of Monographs on Analytical Chemistry and its Applications, vol. 174, 466 pages (2010).
Jiménez, et al., "Glucose sensor based on an amperometric microelectrode with a photopolymerizable enzyme membrane", Sensors and Actuators B, 26-27:421-424 (1995).
Johnson et al., "Reduction of Electrooxidizable Interferent Effects: Optimization of the Applied Potential for Amperometric Glucose Sensors," Electroanalysis, 6, 321-326 (1991).
Klonoff, "A Review of Continuous Glucose Monitoring Technology", Diabetes Technology & Therapeutics, 7(5):770-775 (2005).
Klonoff, "Continuous Glucose Monitoring: Roadmap for 21st century diabetes therapy", Diabetes Care, 28(5):1231-1239 (2005).
Knobbe, et al., "The Extended Kalman Filter for Continuous Glucose Monitoring", Diabetes Technology & Therapeutics, 7(1):15-27 (2005).
Koudelka, et al., "In-vivo Behaviour of Hypodermically Implanted Microfabricated Glucose Sensors", Biosensors & Bioelectronics, 6:31-36 (1991).
Koudelka-Hep, "Electrochemical Sensors for in vivo Glucose Sensing", Biosensors in the Body: Continuous in vivo Monitoring, pp. 57-77 (1997).
Kuure-Kinsey, et al., "A Dual-Rate Kalman Filter for Continuous Glucose Monitoring", Proceedings of the 28th IEEE, EMBS Annual International Conference, pp. 63-66 (2006).
Kvist, et al., "Recent Advances in Continuous Glucose Monitoring: Biocompatibility of Glucose Sensors for Implantation in Subcutis", Journal of Diabetes Science and Technology, 1(5):746-752 (2007).
Lodwig, et al., "Continuous Glucose Monitoring with Glucose Sensors: Calibration and Assessment Criteria", Diabetes Technology & Therapeutics, 5(4):573-587 (2003).
Ming Li, et al., "Implantable Electrochemical Sensors for Biomedical and Clinical Applications: Progress, Problems, and Future Possibilities", Current Medicinal Chemistry, 14:937-951 (2007).
Moatti-Sirat, et al., "Evaluating in vitro and in vivo the interference of ascorbate and acetaminophen on glucose detection by a needle-type glucose sensor", Biosensors and Bioelectronics, 7(5):345-352 (1992).
Morak, et al., "Design and Evaluation of a Telemonitoring Concept Based on NFC-Enabled Mobile Phones and Sensor Devices", IEEE Transactions on Information Technology in Biomedicine, 16(1):17-23 (2012).
Movassaghi, et al., "Wireless Technologies for Body Area Networks: Characteristics and Challenges", IEEE, International Symposium on Communications and Information Technologies (ISCIT), pp. 42-47 (2012).
"Near field communication" retrieved from "http://en.wikipedia.org/w/index.php?title=Near_field_communication&oldid=543740757" on Jun. 27, 2014, 14 pages.

(56) References Cited

OTHER PUBLICATIONS

Nishida, et al., "Development of a ferrocene-mediated needle-type glucose sensor covered with newly designed biocompatible membrane, 2-methacryloyloxyethyl phosphorylcholine-co-n-butyl methacrylate", Medical Progress through Technology, 21:91-103 (1995).
Onuki, et al., "A Review of the Biocompatibility of Implantable Devices: Current Challenges to Overcome Foreign Body Response", Journal of Diabetes Science and Technology, 2(6):1003-1015 (2008).
Palerm, et al., "Hypoglycemia Prediction and Detection Using Optimal Estimation", Diabetes Technology & Therapeutics, 7(1):3-14 (2005).
Poitout, et al., "Calibration in dogs of a subcutaneous miniaturized glucose sensor using a glucose meter for blood glucose determination", Biosensors & Bioelectronics, 7:587-592 (1992).
Rebrin, et al., "Subcutaneous glucose predicts plasma glucose independent of insulin: implications for continuous monitoring", American Journal of Physiology-Endocrinology and Metabolism, 277(3):E561-E571 (1999).
Renard, "Implantable glucose sensors for diabetes monitoring", Min Invas Ther & Allied Technol, 13(2):78-86 (2004).
Rhodes, et al., "Prediction of Pocket-Portable and Implantable Glucose Enzyme Electrode Performance from Combined Species Permeability and Digital Simulation Analysis", Analytical Chemistry, 66(9):1520-1529 (1994).
Robert, "Continuous Monitoring of Blood Glucose", Horm Res 57(suppl 1):81-84 (2002).
Schlosser, et al., "Biocompatibility of Active Implantable Devices", Biosensors in the Body: Continuous in vivo Monitoring, pp. 139-170 (1997).
Schmidt, et al., "Calibration of a wearable glucose sensor", The International Journal of Artificial Organs, 15(1):55-61 (1992).
Schmidtke et al., "Accuracy of the One-Point in Vivo Calibration of "Wired" Glucose Oxidase Electrodes Implanted in Jugular Veins of Rats in Periods of Rapid Rise and Decline of the Glucose Concentration," Anal. Chem., 70, 2149-2155 (1998).
Specification of the Bluetooth System, Experience More, Specification vol. 0, Covered Core Package Version: 4.0, 2302 pages (2010).
Tierney, et al., "Effect of Acetaminophen on the Accuracy of Glucose Measurements Obtained with the GlucoWatch Biographer", Diabetes Technology & Therapeutics, 2(2):199-207 (2000).
Townsend, et al., "Getting Started with Bluetooth Low Energy [Book]", O'Reilly, retrieved from https://www.oreilly.com/library/view/getting-started-with/9781491900550/ch01.html on May 5, 2020, 26 pages.
Velho, et al., "Strategies for Calibrating a Subcutaneous Glucose Sensor", Biomed. Biochim. Acta, vol. 48, pp. 957-964 (1989).
Voskerician, et al., "Sensor Biocompatibility and Biofouling in Real-Time Monitoring", Wiley Encyclopedia of Biomedical Engineering, (John Wiley & Sons, Inc.), pp. 1-19 (2006).
Ward, "A Review of the Foreign-body Response to Subcutaneously-implanted Devices: The Role of Macrophages and Cytokines in Biofouling and Fibrosis", Journal of Diabetes Science and Technology, 2(5):768-777 (2008).
Ward, et al., "A new amperometric glucose microsensor: in vitro and short-term in vivo evaluation", Biosensors & Bioelectronics, 17:181-189 (2002).
Yang, et al., "Glucose Biosensors Based on Oxygen Electrode with Sandwich-Type Membranes", Annals of Biomedical Engineering, 23:833-839 (1995).
Yang, et al., "Glucose Biosensors with Enzyme Entrapped in Polymer Coating", Biomedical Instrumentation & Technology, 29(2):125-133 (1995).
Chen, et al., "A novel fault-tolerant sensor system for sensor drift compensation", Sensors and Actuators, A 147:623-632 (2008).
FreeStyle Navigator Continuous Glucose Monitoring System, Summary of Safety and Effectiveness Data in support of Pre-Market Approval (PMA) No. P050020, Abbott Diabetes Care, 27 pages (2008).
FreeStyle Navigator Continuous Glucose Monitoring System, User Guide, Abbott Diabetes Care Inc., 195 pages (2008).
Gerritsen, et al., "Performance of subcutaneously implanted glucose sensors for continuous monitoring", The Netherlands Journal of Medicine, 54:167-179 (1999).
Guardian® Real-Time, Continuous Glucose Monitoring System, User Guide, Medtronic MiniMed, Inc., 181 pages (2006).
Guardian® RT, Continuous Glucose Monitoring System, REF MMT-7900, User Guide, Medtronic MiniMed, 128 pages (2005).
Heller, et al., "Electrochemical Glucose Sensors and Their Applications in Diabetes Management", Chemical Reviews, 108(7):2482-2505 (2008).
Kalivas, et al., "Compensation for Drift and Interferences in Multicomponent Analysis", Laboratory for Chemometrics, Department of Chemistry, University of Washington, 38 pages (1982).
Thévenot, et al., "Electrochemical Biosensors: Recommended Definitions and Classification (Technical Report)", Pure Appl. Chem. 71(12):2333-2348 (1999).
U.S. Appl. No. 12/842,013 Office Action dated Aug. 26, 2015.
U.S. Appl. No. 12/842,013 Office Action dated Mar. 23, 2016.
U.S. Appl. No. 12/842,013 Office Action dated Nov. 6, 2014.
Walt, et al., "The chemistry of enzyme and protein immobilization with glutaraldehyde", Trends in Analytical Chemistry, 13(10):425-430 (1994).
Zhang, "Investigations of potentially implantable glucose sensors", University of Kansas, 24 pages (1991).
U.S. Appl. No. 60/687,199, filed Jun. 2, 2005, Ward, et al.
U.S. Appl. No. 61/155,889, filed Feb. 26, 2009, Hoss, et al.
Atanasov, et al., "Implantation of a refillable glucose monitoring-telemetry device", Biosensors & Bioelectronics, 12(7):669-680 (1997).
Bindra, "Development of potentially implantable glucose sensors", The University of Arizona, 227 pages (1990).
FreeStyle Navigator Continuous Glucose Monitoring System, User's Guide, Abbott Diabetes Care Inc., 38 pages (2008).
Guardian® Real-Time, Continuous Glucose Monitoring System, User Guide, Medtronic MiniMed, Inc., 184 pages (2006).
Kerner, et al., The function of a hydrogen peroxide-detecting electroenzymatic glucose electrode is markedly impaired in human sub-cutaneous tissue and plasma, Biosensors & Bioelectronics, 8:473-482 (1993).
Koschinsky, et al., "Sensors for glucose monitoring: technical and clinical aspects", Diabetes/Metabolism Research and Reviews, 17:113-123 (2001).
Koschwanez, et al., "In vitro, in vivo and post explantation testing of glucose-detecting biosensors: Current methods and recommendations", Biomaterials, 28:3687-3703 (2007).
Moussy, et al. "Performance of Subcutaneously Implanted Needle-Type Glucose Sensors Employing a Novel Trilayer Coating", Anal. Chem., 65:2072-2077 (1993).
Pickup, et al., "In vivo glucose sensing for diabetes management: progress towards non-invasive monitoring", BMJ, 319, pp. 1-4 (1999).
Pickup, et al., "Responses and calibration of amperometric glucose sensors implanted in the subcutaneous tissue of man", Acta Diabetol, 30:143-148 (1993).
Ward, et al., "Rise in background current over time in a subcutaneous glucose sensor in the rabbit: relevance to calibration and accuracy", Biosensors & Bioelectronics, 15:53-61 (2000).
Wilson, et al., "Biosensors for real-time in vivo measurements", Biosensors and Bioelectronics, 20:2388-2403 (2005).
Wisniewski, et al., "Analyte flux through chronically implanted subcutaneous polyamide membranes differs in humans and rats", Am J Physiol Endocrinol Metab, 282:E1316-E1323 (2002).
"Abbott Receives CE Mark for Freestyle® Libre, A Revolutionary Glucose Monitoring System for People with Diabetes," 8 pages (2023).
ATTD Program, 4 pages (2009).
Boise, Interview with Dexcom CEO, Dexcom CEO Kevin Sayer EXplains G6, 9 pages (2018).
Dexcom (DXCM) Company Profile, 2017 /Q4 Earnings call transcript, 12 pages (2017).

(56) References Cited

OTHER PUBLICATIONS

Dexcom G6 Continuous Glucose Monitoring System User Guide, 7 pages (2020).
Email communication from Sophie Hood, Jan. 24, 2023, 6 pages.
Hall, Interview with Kevin Sayer, President and CEO of Dexcom About the New Dexcom G6, College Diabetes Network, 6 pages (2021).
Hoss et al., "Continuous glucose monitoring in the tissue: Do we really need to calibrate in-vivo?," Diabetes Technology & Therapeutics, vol. 11, No. 2, (2009).
Omnipod image, Exhibit 182, 2 pages, Sep. 22, 2022.
Sayer, CGMS Changing Diabetes Management: Kevin Sayer, DIC Interview Transcript, Featuring Steve Freed, 11 pages (2019).
S&P Global Market Intelligence "DexCom, Inc. NasdaqGS:DXCM, Company Conference Presentation," 17 pages (2021).
S&P Global Market Intelligence "DexCom, Inc. NasdaqGS:DXCM, Company Conference Presentation," 10 pages (2020).
S&P Global Market Intelligence "DexCom, Inc. NasdaqGS:DXCM, Company Conference Presentation," 11 pages (2019).
Sonix, Dexcom CEO—Prime Position in Our Market—Mad Money—CNBC.mp4, 4 pages (2023).
U.S. Food & Drug Administration, "Deciding When to Submit a 510(k) for a Change to an Existing Device, Guidance for Industry and Food and Drug Administration Staff," 78 pages (2017).
U.S. Food & Drug Administration, "Deciding When to Submit a 510(k) for a Software Change to an Existing Device, Guidance for Industry and Food and Drug Administration Staff," 32 pages (2017).
Watkin, "An Introduction to Flash Glucose Monitoring," 16 pages (2013).

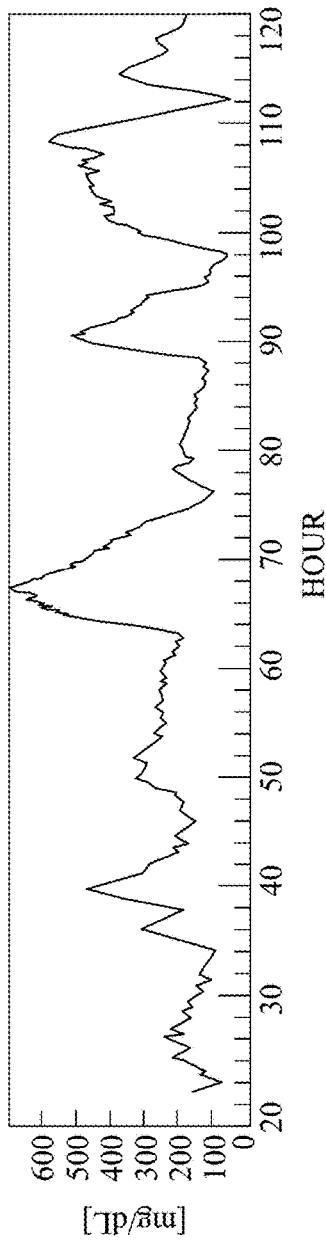
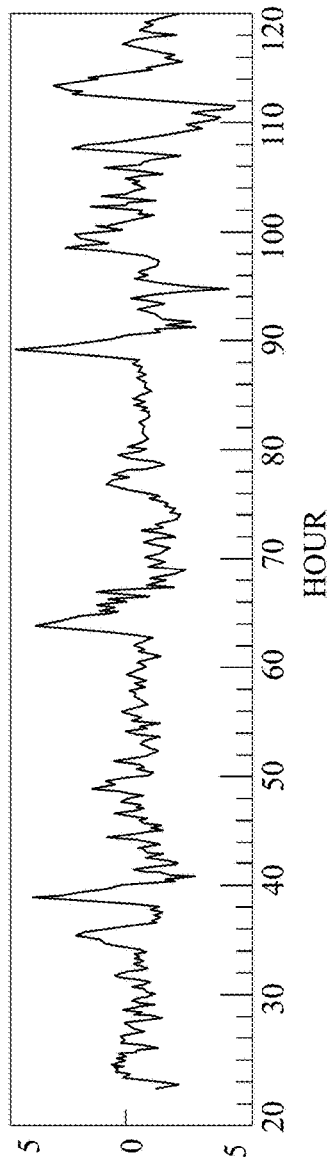
FIG. 7A
FIG. 7B
FIG. 7C

METHOD AND APPARATUS FOR IMPROVING LAG CORRECTION DURING IN VIVO MEASUREMENT OF ANALYTE CONCENTRATION WITH ANALYTE CONCENTRATION VARIABILITY AND RANGE DATA

PRIORITY

The present application is a continuation of U.S. patent application Ser. No. 15/910,927 filed Mar. 2, 2018, now allowed, which is a continuation of U.S. patent application Ser. No. 14/431,168 filed Mar. 25, 2015, now U.S. Pat. No. 9,907,492, which is a national stage patent application under 35 U.S.C. § 371, which claims priority to PCT Application No. PCT/US13/60471 filed Sep. 18, 2013, which claims priority to U.S. Provisional Application No. 61/705,929 filed Sep. 26, 2012, entitled "Method and Apparatus for Improving Lag Correction During In Vivo Measurement of Analyte Concentration with Analyte Concentration Variability and Range Data", the disclosures of each of which are incorporated herein by reference in their entirety for all purposes.

BACKGROUND

The detection of the concentration level of glucose or other analytes in certain individuals may be vitally important to their health. For example, the monitoring of glucose levels is particularly important to individuals with diabetes or pre-diabetes. People with diabetes may need to monitor their glucose levels to determine when medication (e.g., insulin) is needed to reduce their glucose levels or when additional glucose is needed.

Devices have been developed for automated in vivo monitoring of analyte concentrations, such as glucose levels, in bodily fluids such as in the blood stream or in interstitial fluid. Some of these analyte level measuring devices are configured so that at least a portion of the devices are positioned below a skin surface of a user, e.g., in a blood vessel or in the subcutaneous tissue of a user. As used herein, the term analyte monitoring system is used to refer to any type of in vivo monitoring system that uses a sensor disposed with at least a portion subcutaneously to measure and store sensor data representative of analyte concentration levels automatically over time. Analyte monitoring systems include both (1) systems such as continuous glucose monitors (CGMs) which transmit sensor data continuously or at regular time intervals (e.g., once per minute) to a processor/display unit and (2) systems that transfer stored sensor data in one or more batches in response to a request from a processor/display unit (e.g., based on an activation action and/or proximity, for example, using a near field communications protocol) or at a predetermined but irregular time interval.

Determining an analyte concentration level in blood based on the analyte concentration in interstitial fluid can be difficult because changes of the analyte concentration levels in interstitial fluid typically lags behind changing analyte concentration levels in blood. Thus, what is needed are systems, methods, and apparatus to correct for the time lag between blood analyte level changes and interstitial fluid analyte level changes.

SUMMARY

Methods, devices, and systems are provided for correcting time lag in measurements of analyte concentration level in interstitial fluid. When applied to lag correction of glucose using analyte monitoring system (e.g., CGM) sensor data measuring glucose in interstitial fluid, the degree of glycemic variability and/or range are used to determine the relative benefit of relying on the computed glucose rate of change for lag correction versus the risk of reduced precision caused by amplifying noise and other artifacts. Thus, in some embodiments, the invention includes determining the analyte concentration variability of a patient and/or the analyte concentration range of a patient and determining a lag correction value to apply to sensor data representative of analyte concentration measured in interstitial fluid using an analyte measurement system. The lag correction value is adjusted based upon the analyte concentration variability and/or analyte concentration range. Finally, an analyte concentration level representative of the blood analyte concentration level is computed based on the adjusted lag correction value. Related systems and computer program products are also disclosed.

In some embodiments, the invention includes receiving a signal representative of sensor data from an analyte monitoring system related to an analyte level of a patient measured over time. Rates of change of the sensor data for a time period of the sensor data are computed along with a rate distribution of the rates of change. The rate distribution is transformed into a linear arrangement, a best-fit line is determined for the transformed rate distribution, a slope of the best-fit line is computed, and a scaling factor for lag correction is determined. The slope of the best-fit line is used as a representation of the variability of the analyte level to adjust an amount of lag correction applied to the sensor data by adjusting the scaling factor for lag correction. Related systems and computer program products are also disclosed.

Some other embodiments of the present disclosure include computer-implemented methods of correcting lag in measurements of analyte concentration level in interstitial fluid. The methods include defining a scaling factor for lag correction, collecting a moving window of historical analyte sensor data, defining a probability density function of the sensor data within the moving window, determining a normalized analyte variability ratio, storing the normalized analyte variability ratio computed at regular intervals, comparing a latest normalized analyte variability ratio to a predetermined value and a number of prior values, setting a value of the scaling factor based on the probability density function, and computing lag corrected values based on the scaling factor. Related systems and computer program products are also disclosed.

Yet other embodiments of the present disclosure include additional and alternative methods of correcting lag in measurements of analyte concentration level in interstitial fluid. The methods include determining at least one of analyte concentration variability of a patient and analyte concentration range, determining a lag correction value to apply to sensor data representative of analyte concentration measured in interstitial fluid using an analyte measurement system, adjusting the lag correction value based upon the at least one of analyte concentration variability and analyte concentration range, and computing an analyte concentration level representative of a blood analyte concentration level based on the adjusted lag correction value. Related systems and computer program products are also disclosed.

Numerous other aspects and embodiments are provided. Other features and aspects of the present invention will become more fully apparent from the following detailed description, the appended claims, and the accompanying drawings.

BRIEF DESCRIPTION OF THE DRAWINGS

FIGS. 7A to 7C depict plots of example glucose levels over time, corresponding rate of change of the glucose levels over time, and best-fit lines of the corresponding transformed glucose concentration rate of change distribution, respectively and in accordance with some embodiments of the present invention.

DETAILED DESCRIPTION

Figure 1:
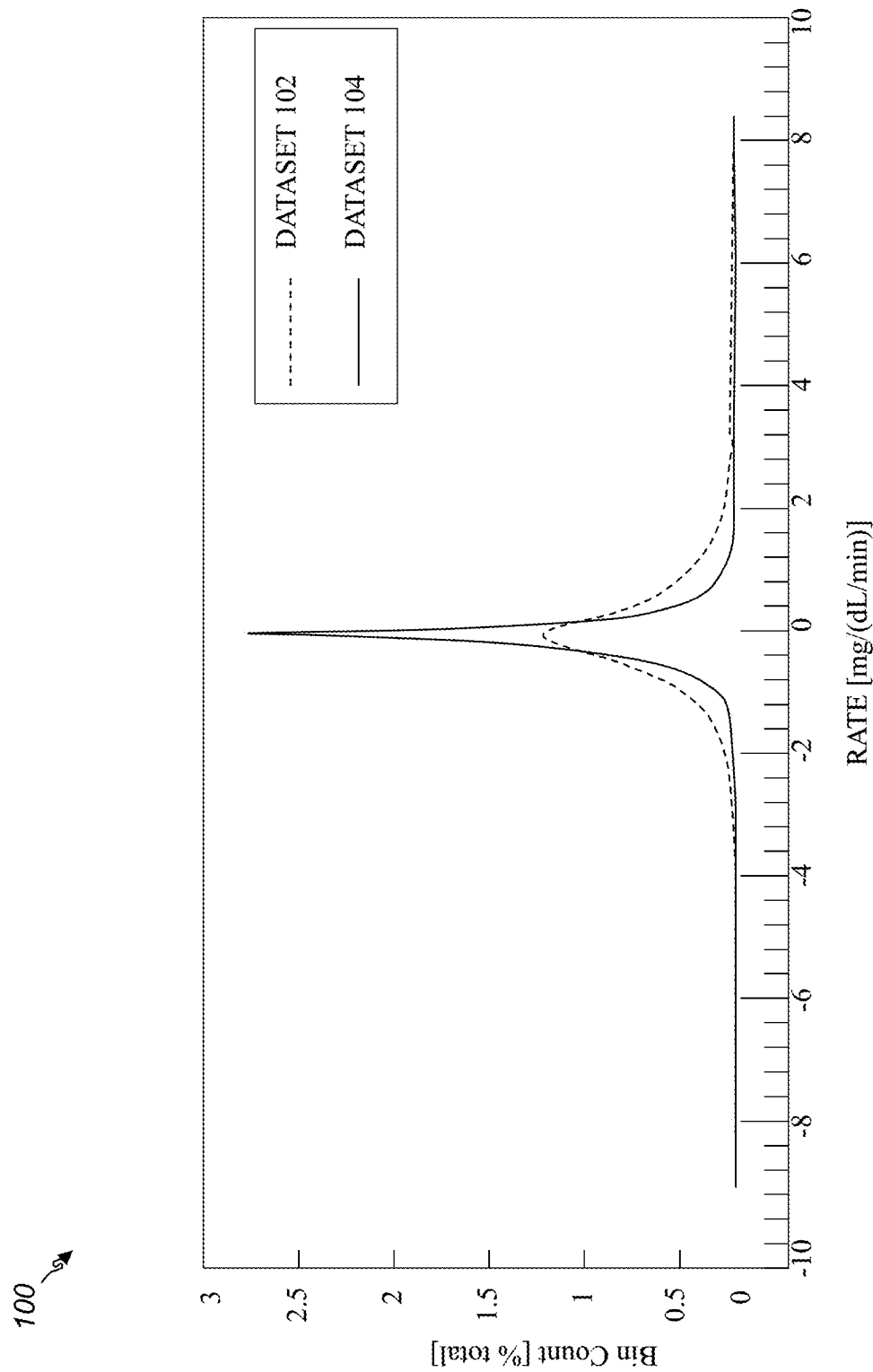
FIG. 1 depicts a plot of an example analyte concentration rate of change distribution in accordance with some embodiments of the present invention.

The present invention provides systems, methods, and apparatus to improve lag correction in devices that determine analyte concentration in the blood via measurement of the analyte concentration in interstitial fluid. For such devices, determining blood glucose levels, for example, may involve performing lag correction based on a calculated estimate of rates of change of blood glucose levels. However, the accuracy of computing the rates of change can be very sensitive to noise. It has been observed that in patients with relatively good glycemic control (i.e., relatively low blood glucose level variability), the relative performance improvement due to lag correction is not as significant as in subjects with poorer control (i.e., relatively high blood glucose level variability). In some cases, the risk of reduced accuracy due to rate calculation error increases because a higher fraction of the computed rate is due to noise and other artifacts.

Improving lag correction is thus a tradeoff between maximal smoothing (i.e., increasing precision) during periods of noisy, unchanging levels and maximal lag correction (i.e., increasing accuracy) during periods of non-noisy, rapidly changing levels. Therefore, given a constant noise level, a relatively unchanging glucose level benefits from less lag correction than a relatively rapidly changing glucose level. Existing methods of lag correction may rely on estimating the glucose level trend and minute-by-minute noise level to determine the amount of smoothing to apply. In contrast, the present invention uses information beyond the time span in which the signals are still highly correlated, to get a more global sense of the patient's glucose level variability.

In some embodiments, the present invention considers rates of change of glucose concentration levels based on glucose measurements over time and assesses the degree of glucose level variability that is relatively insensitive to noise and other artifacts. The degree of glucose level variability is usable in several ways. In some embodiments, the degree of glucose level variability is used to help determine the amount of tradeoff between maximizing lag correction of interstitial glucose measurements and minimizing output noise. In some embodiments, the degree of glucose level variability is being used to aid in measuring a patient's degree of glycemic control.

In addition to considering the rate of change of glucose levels, considering the range of a patient's glucose levels can also be used to improve lag correction according to the present invention. The factors that reduce precision affect lag correction more at the extreme ends of a patient's glucose excursion. For example, at the lower end of a patient's glucose levels, the levels can be affected by dropouts and other signal artifacts in a higher percentage than at the higher end. In other words, a 30 mg/dL dropout at a 60 mg/dL glucose level is a 50% error while the same 30 mg/dL dropout at a 180 mg/dL level is only a 17% error. As a result, the risk of introducing error when lag correcting to the full extent differs in these different glucose level ranges. Thus, considering the range of a patient's glucose levels and the patient's level patterns can be used to relate the risk of making a lag correction and the factors that reduce precision.

Since a patient's glucose levels do not regularly follow a repetitive pattern and patients have different patterns that can change over time, a static plot of a patient's glucose response to a meal, for example, is not likely to be useful for gauging the range of a patient's glucose levels. However, by starting with conservative nominal values and storing glucose variability and excursion range statistics computed from measurements taken over a period of time (e.g., a window of hours or days), a more accurate characterization of the patient's changing glucose range can be determined. Using this slowly changing range, the relative position of the most recently measured glucose level compared to the patient's history can be determined. When the most recently measured glucose value is in the lower range of the patient's historic range, then the amount of lag correction applied can be reduced by a predetermined amount as a function of the most recently measured glucose value and one or more slowly changing statistics collected from historical sensor data of the patient. When the most recently measured glucose value is in the middle range of the patient's historic range, the amount of lag correction applied can be set to the maximum. At the higher range of the historic range, the amount of lag correction can be reduced as with the lower range. Thus, in this manner, the amount of lag correction can be reduced at the extremes of the patient's glucose excursions.

Embodiments of the invention are described primarily with respect to continuous glucose monitoring devices and systems but the present invention can be applied to other analytes, other analyte characteristics, and other analyte measurement systems, as well as data from measurement systems that transmit sensor data from a sensor unit to another unit such as a processing or display unit in response to a request from the other unit. For example, other analytes that can be monitored include, but are not limited to, acetyl choline, amylase, bilirubin, cholesterol, chorionic gonadotropin, creatine kinase (e.g., CK-MB), creatine, DNA, fructosamine, glutamine, growth hormones, hormones, ketones, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, can also be monitored. In those embodiments that monitor more than one analyte, the analytes can be monitored at the same or different times. In addition, in some embodiments, the present invention can be applied to non-analyte sensor data. For example, non-analyte sensor data can include temperature estimation of a target physiological compartment that is made based on measuring the temperature of a nearby compartment, where the measured temperature lags from the temperature of the target compartment. The present invention also provides numerous additional embodiments.

Some embodiments of the present invention include a programmed computer system adapted to receive and store data from an analyte monitoring system. The computer system can include one or more processors for executing instructions or programs that implement the methods described herein. The computer system can include memory and persistent storage devices to store and manipulate the instructions and sensor data received from the analyte monitoring system. The computer system can also include communications facilities (e.g., wireless and/or wired) to enable transfer of the sensor data from the analyte monitoring system to the computer. The computer system can include a display and/or output devices for identifying dropouts in the sensor data to a user. The computer system can include input devices and various other components (e.g., power supply, operating system, clock, etc.) that are typically found in a conventional computer system. In some embodiments, the computer system is integral to the analyte monitoring system. For example, the computer system can be embodied as a handheld or portable receiver unit within the analyte monitoring system.

In some embodiments, the various methods described herein for performing one or more processes, also described herein, can be embodied as computer programs (e.g., computer executable instructions and data structures). These programs can be developed using an object oriented programming language, for example, that allows the modeling of complex systems with modular objects to create abstractions that are representative of real world, physical objects and their interrelationships. However, any practicable programming language and/or techniques can be used. The software for performing the inventive processes, which can be stored in a memory or storage device of the computer system described herein, can be developed by a person of ordinary skill in the art based upon the present disclosure and can include one or more computer program products. The computer program products can be stored on a non-transitory computer readable medium such as a server memory, a computer network, the Internet, and/or a computer storage device.

Turning now to FIG. 1, two glucose rates of change distributions from two sensor data datasets are plotted in graph 100. The glucose rates of change are computed from sensor data (e.g. from an analyte measurement system) over all available points in a dataset. Smoothing between values can be performed to improve distribution uniformity. Dataset 102 is taken from measurements of patients with diabetes (PwD) and dataset 104 is taken from measurements of patients without diabetes (PwoD). As can be expected, the glucose rates of change of the PwoD are more concentrated in the middle area, corresponding to a slow/no rate of change, as compared to the distribution of the PwD data. Note that the present invention uses a relatively large number of glucose values (e.g., sensor data) in order to obtain a useful rate distribution metric. In the case of self-monitored blood glucose measurement via an in vitro glucose meter, this may mean taking frequent enough finger stick values over the course of many hours. In the case of an in vivo analyte monitoring system that collects sensor data (such as a CGM or other type of sensor glucose monitor), a significantly shorter data collection duration can suffice.

Figure 2:
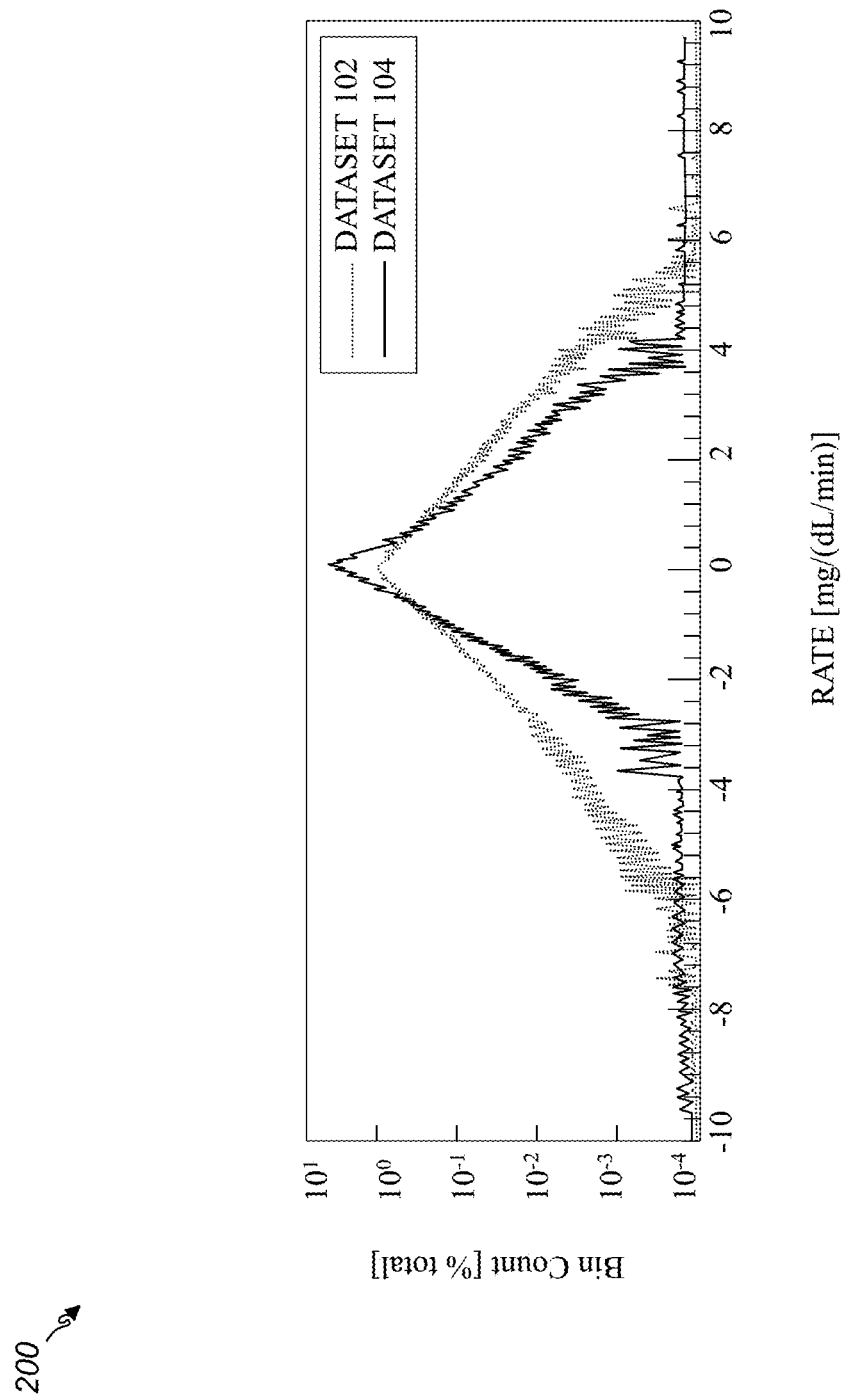
FIG. 2 depicts a plot of an example transformed analyte concentration rate of change distribution in accordance with some embodiments of the present invention.

FIG. 2 depicts glucose rate of change distribution from the same datasets 102, 104 shown in FIG. 1, with the distribution count (on the y-axis) shown on a logarithmic scale in graph 200. Note that the distinction in glucose variability between PwD and PwoD can be more clearly discerned over a wider range of rates of change. Unlike FIG. 1, the transformed distribution is shaped such that a simple linear fit could be performed on each direction of the rates of change. The slope of this best fit line reflects the tightness of the distribution of the rates of change. The steeper the absolute slope, the tighter the distribution.

Figure 3:
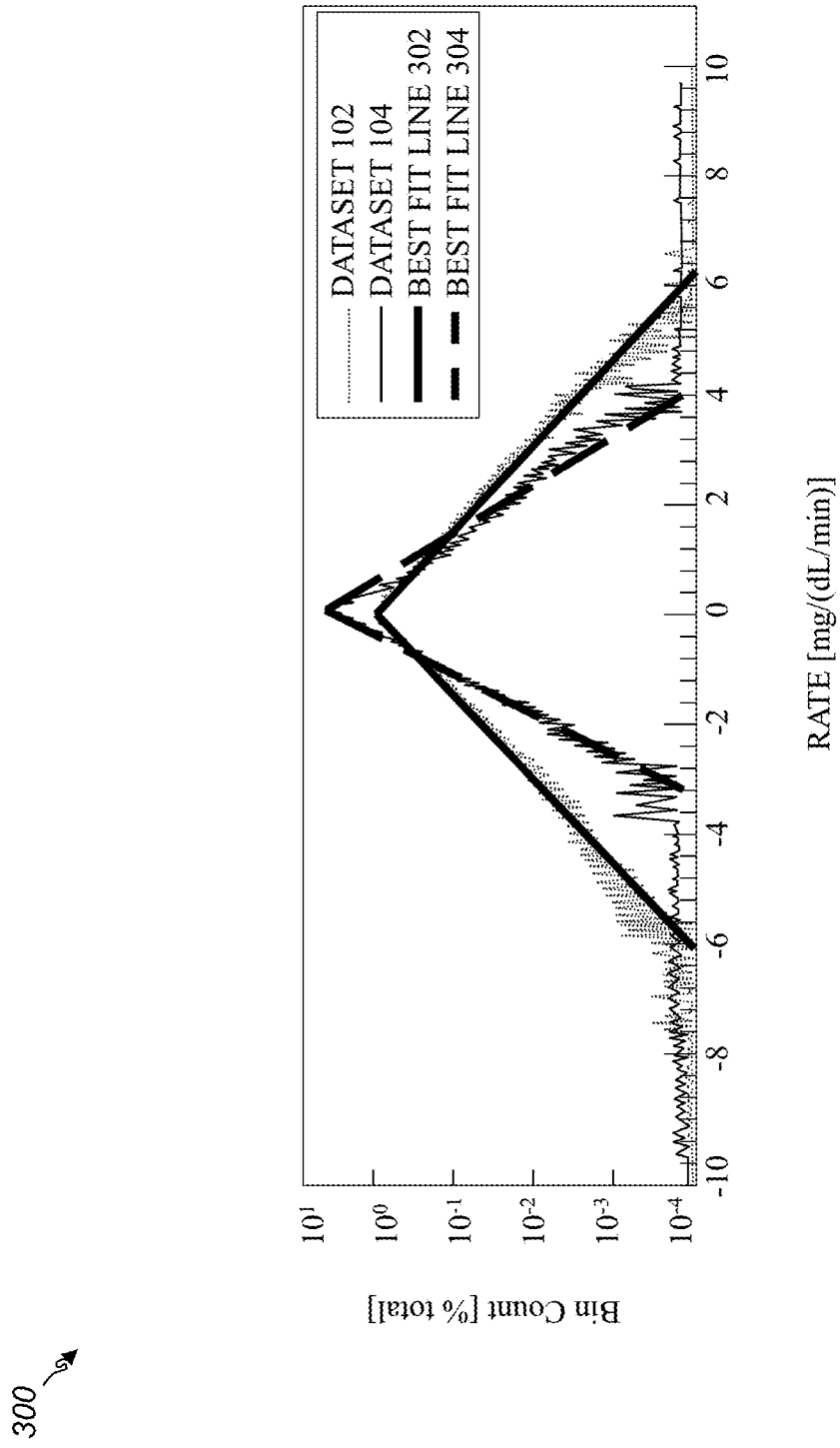
FIG. 3 depicts a plot of example best-fit lines of a transformed analyte concentration rate of change distribution in accordance with some embodiments of the present invention.

FIG. 3 illustrates the same transformed distributions as FIG. 2 but with a straight thick solid line representing the best-fit line 302 for the PwD rate distribution and a straight thick dashed line representing the best-fit line 304 for the PwoD rate distribution in graph 300. The slope of the best-fit line 304 taken from the transformed PwoD rate distribution dataset 104 is much steeper than that of the best-fit line 302 corresponding to the transformed PwD rate distribution dataset 102. Similarly, patients with diabetes who maintain a better glycemic control level will have best-fit lines with steeper slopes compared to patients with diabetes with a poorer glycemic control level.

Figure 4:
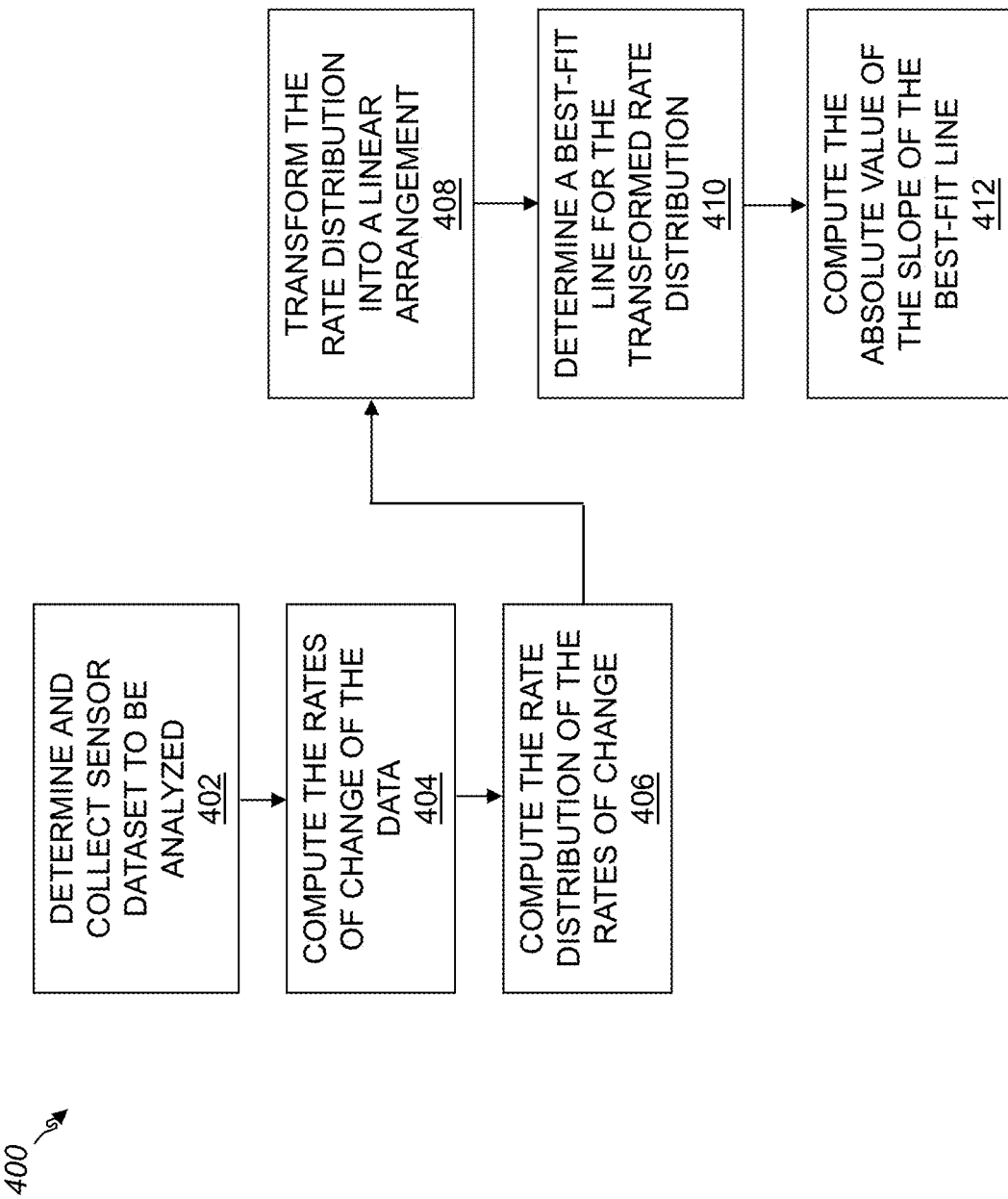
FIG. 4 depicts a flowchart illustrating an example of a method of determining glucose variability in accordance with some embodiments of the present invention.

Turning now to FIG. 4, a flowchart depicting an example method 400 according to embodiments of the present invention is provided. Sensor data is collected using an analyte measurement system (e.g., a continuous glucose monitor) (402). In some embodiments, the sensor data is calibrated and/or scaled into glucose concentration units. Note that the method 400 can be applied to sensor data that is currently being received from an analyte measurement system (e.g., a real-time application) and/or to stored sensor data that was previously received (e.g., a retrospective application). For a real-time implementation, sensor data is collected within a moving time window of a fixed period starting at a point in the past up to the present time. For a retrospective implementation, stored sensor data is used in a moving time window of a fixed period starting at a point in the past up to a future point in time.

Once the dataset is defined, the rates of change of the data are computed (404). In other words, for each analyte level measurement, relative to a prior measurement, the amount of change in the analyte concentration level per unit time is computed. Next, based on the computed rates of change of the data, the rate distribution of the rates of change are computed (406). In some embodiments, the distribution of the rates of change are being plotted as shown in FIG. 1 described above. The y-axis of the distribution of the rates of change can then be transformed into a logarithmic scale (408) as shown in FIG. 2 described above. In some embodiments, different scales/transforms are used. For example, instead of a logarithmic scale, a power scale, a square-root scale, or other scale is used to transform the plot of the distribution to taper off from zero rate in a linear fashion. The example in FIG. 2 uses a base-ten, logarithmic transformation. Other base values can also be used. Once a transformation that renders the distribution in a linear manner has been found and computed, a best-fit line is determined, e.g., for both positive and negative rate sides of the transformed distribution (410). For example, the best-fit line can be determined using a common "least-squares error" fit method, an orthogonal fit method, a method of averages, or other well-known methods. Examples of best-fit lines for the positive and negative rates are illustrated in FIG. 3. In some embodiments, the absolute value of the slopes of the positive and negative rate sides of the transformed distribution are then calculated (412). These values represent a simple objective measure of the variability of the analyte concentration and can be used in various applications as mentioned above and described in more detail below.

Figure 5:
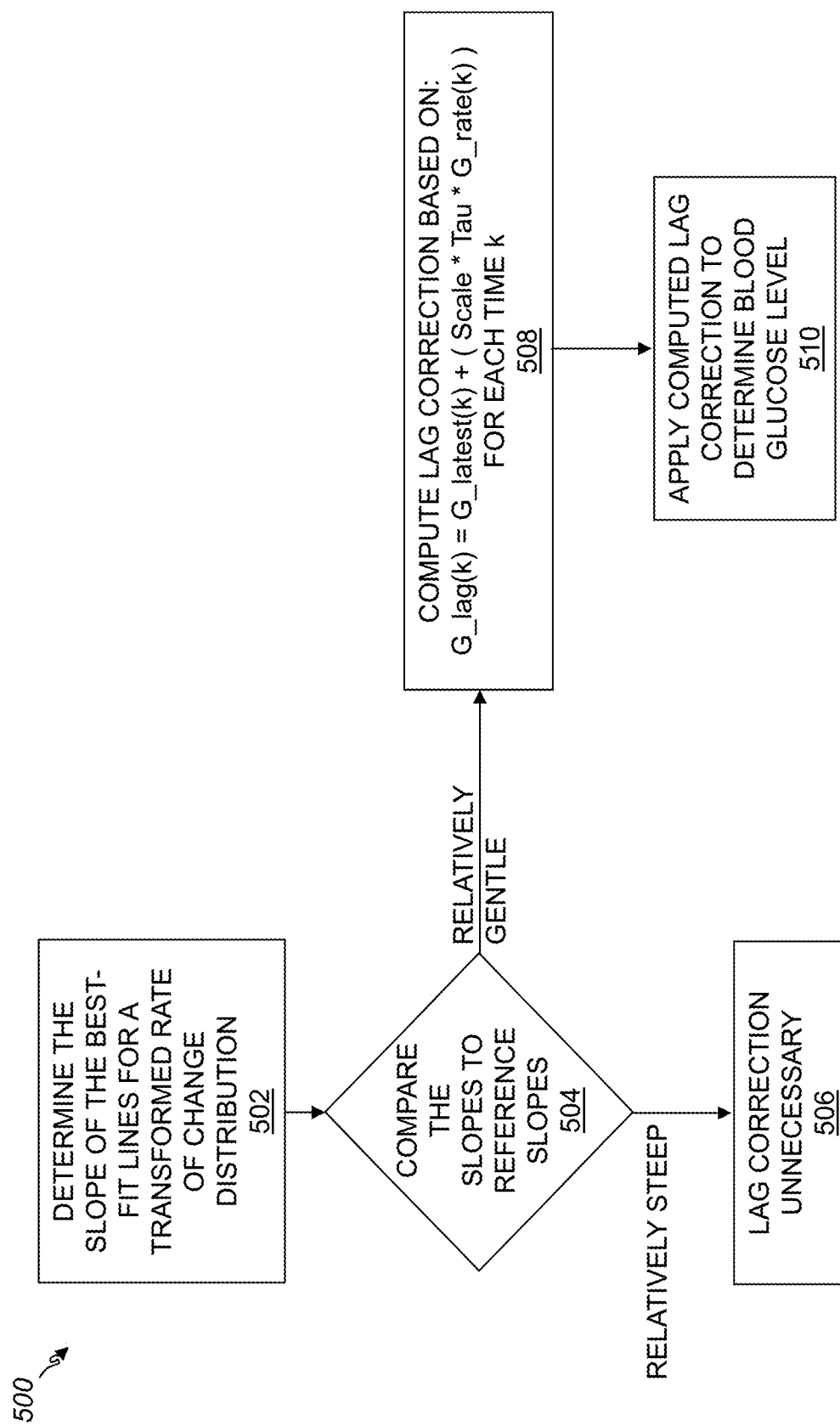
FIG. 5 depicts a flowchart illustrating an example of a method of lag correction based on glucose variability in accordance with some embodiments of the present invention.

When applied to lag correction of glucose using analyte monitoring system (e.g., CGM) sensor data measuring glucose in interstitial fluid, the degree of glycemic variability can be used to determine the relative benefit of relying on the computed glucose rate of change for lag correction versus the risk of reduced precision caused by amplifying noise and other artifacts. The method 500 of determining how much lag correction to apply is described with reference to the flowchart of FIG. 5. Using the method 400 of FIG. 4 described above, the absolute value of the slopes of the positive and negative rate sides of a transformed rate of change distribution are determined (502). The slopes are compared to one or more reference slopes (504). A predetermined reference slope can be used. The units of this slope are arbitrary and are influenced by the choice of the transformation function. For example, using a logarithmic transformation function, the base can be tuned such that the absolute value of the reference slope equals a convenient integer, such as 2. Other values for a predetermined reference slope can be used. In some embodiments, the slopes can additionally or alternatively be compared to the slopes of sensor data collected from prior time periods.

If the latest slope is relatively steep, then the glucose variability is relatively low. In this case, lag correction is relatively unnecessary (506). Conversely, if the latest slope is gentle (i.e., not steep) compared to the reference, lag correction becomes relatively more important and the method proceeds to compute a correction (508). Depending on a separately determined noise metric, the amount of lag correction applied can vary from 0 to 100%. The noise metric is directly related to the variability of the rate of change calculation, G_rate. If G_rate is calculated from an average of first differences of glucose values in a predetermined window of time, say for example, 15 minutes, then one noise metric can be calculated by taking the standard deviation of the first difference values in that window. For example, in some embodiments, the amount of lag correction to apply is determined (508) based upon the following equation:

$$G\_lag(k) = G\_latest(k) + (K^*\tau^*G\_rate(k))  \quad \text{(Equation 1)}$$

where G_latest(k) represents the latest interstitial glucose estimate at time k, K represents a scaling factor that determines the amount of lag correction necessary, varying from 0 to 1. The scale K is determined based on two components: a comparison of the computed slope against a reference slope (504) and the noise metric. For example, suppose the slope comparison generates a ratio Rs, and the noise metric generates a ratio N. The slope comparison ratio Rs approaches zero for gentle slopes, and approaches one for steep slopes. The noise metric N approaches one as the sensor signal becomes noisier, and approaches zero otherwise. Then, the scale K can be computed as a product of Rs and N. Alternatively, the scale K can be computed as the smaller of Rs or N. Tau ($\tau$) represents the assumed time constant of lag correction, computed a priori based on population data, and G_rate(k) represents the computed glucose rate of change at time k. Thus, for an unchanging noise characteristic, a relatively steep glucose rate of change distribution slope results in a lower value of scale K. A relatively gentle glucose rate of change distribution slope results in a higher value of scale K. When glucose levels are not changing by a significant amount due to relatively good glycemic control, the risk of reducing precision (i.e., increasing noise) may outweigh the benefit of increasing accuracy (i.e., reducing lag) in the process of lag correcting in the presence of a certain level of signal noise. The calculated lag correction for each time k is applied to the measured interstitial fluid glucose level to more accurately represent the patient's blood glucose level at each time k (510).

Figure 6:
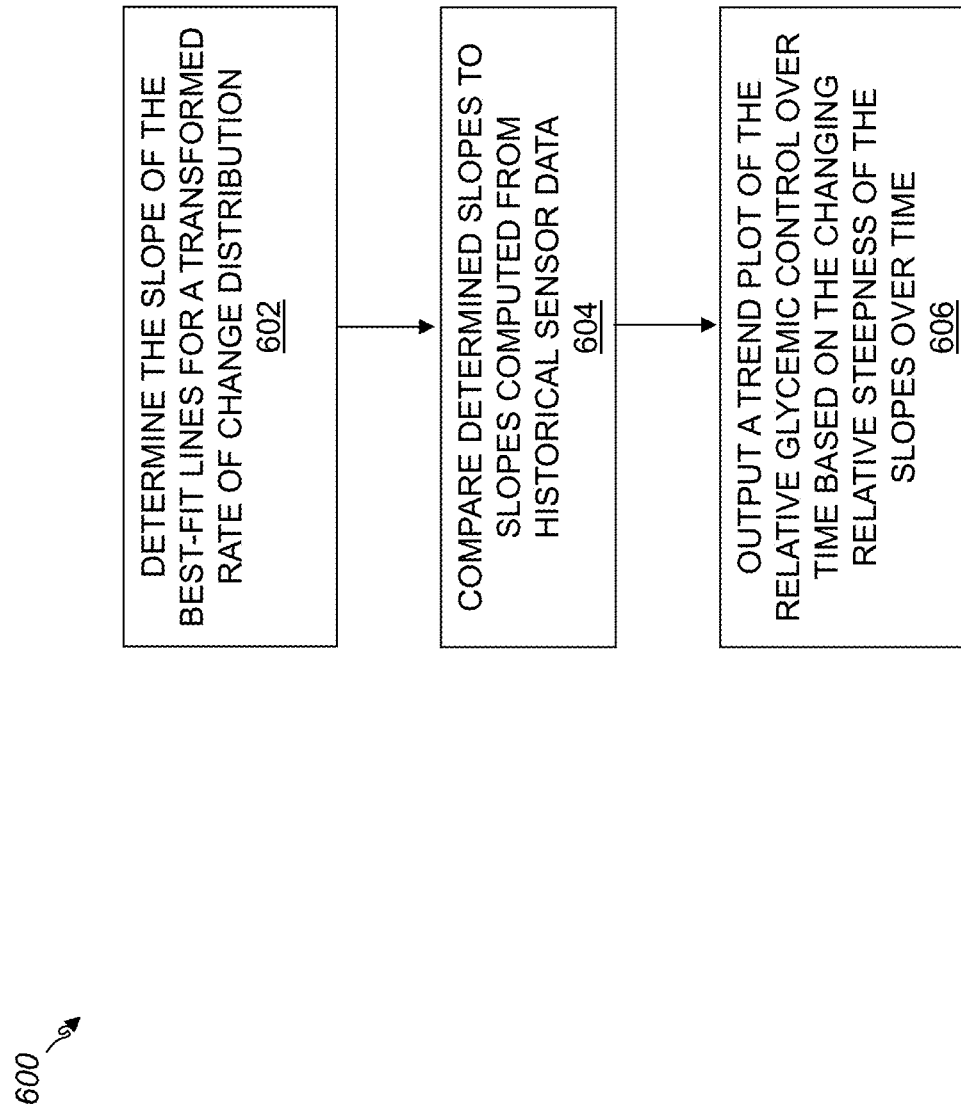
FIG. 6 depicts a flowchart illustrating an example of a method of monitoring glycemic control based on glucose variability in accordance with some embodiments of the present invention.

In other embodiments, the degree of glycemic variability is used to assess glycemic control for diabetes treatment evaluation, treatment adjustment, or other purposes. For example, a method 600 of monitoring glycemic control is implemented as depicted in the flowchart of FIG. 6. Using the method 400 of FIG. 4 described above, the absolute value of the slopes of the positive and negative rate sides of a transformed rate of change distribution are determined (602). In some embodiments, the slopes are then compared to a record of slopes computed from historic sensor data stored from prior uses of an analyte monitoring system (604). For example, a database that stores transformed plots of rate of change distributions and corresponding best-fit lines for different "wears" of an analyte monitoring system sensor can be used to determine the relative steepness and thus, the relative amount of glycemic control of the patient compared to their past performance. A trend plot of relative glycemic control over time can be graphed and output by the system (606).

Turning to FIGS. 7A to 7C, graphs 700, 702, 704 are provided representing example data collected from a patient with relatively poor glycemic control. A glucose level plot 700 over time in FIG. 7A shows a relatively high mean glucose level and indicates that a significant amount of time is spent with the glucose level changing in value. The rate of change plot 702 in FIG. 7B confirms this given the significant variance from the zero line. The transformed plot 704 of the distribution of the rate of change in FIG. 7C further confirms this observation as reflected by the slopes of the best fit lines 706, 708.

The positive rate slope 708 is steeper than the negative rate slope 706, as also indicated by the relatively faster glucose level increases compared to the decrease towards lower glucose levels. In some embodiments, the relative steepness of the positive and negative rate distributions can also be used to refine the patient's treatment regimen. For example, by adjusting the lead-time between pre-prandial bolus and actual meals, the glucose level increase can be tempered down. In addition, by changing the timing and amount of correction bolus to allow for a faster initial postprandial glucose recovery followed by a smaller correction bolus later on, a softer "landing" towards normoglycemia can be achieved.

In addition to using glycemic variability to inform the decision whether to apply lag correction, the glycemic range can also be useful in avoiding amplifying noise and artifacts in the sensor data. As mentioned above, at the low glucose range, the presence of signal artifacts such as dropouts significantly impact real-time lag correction of glucose levels measured by the analyte monitoring system. As a patient's level of glycemic control varies over time, their glucose range (i.e., max, min, median glucose levels) varies. When glycemic control is relatively good, the ratio between rate calculation error and true rate is typically larger than when glycemic control is relatively poor. Thus, according to the present invention, the extent of lag correction is scaled back during critical conditions (e.g., such as the patient's glucose level being in the low range), by using historical glucose levels to determine the likelihood of conditions that warrant scaling back of lag correction.

Figure 8:
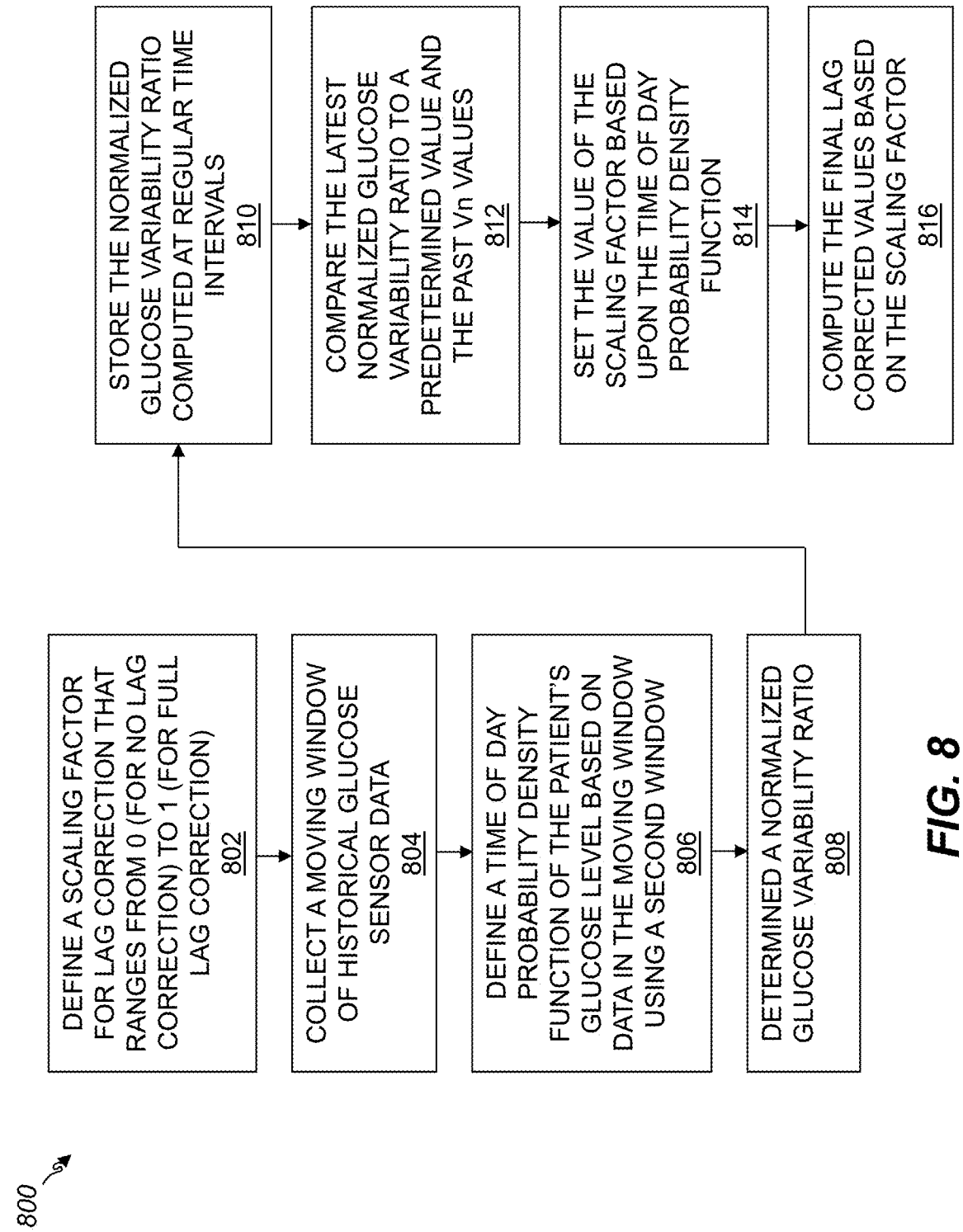
FIG. 8 depicts a flowchart illustrating an example of a method of lag correction based on glucose range in accordance with some embodiments of the present invention.

Turning now to FIG. 8, a method 800 for determining an amount of lag correction to apply to sensor data from glucose measurement of interstitial fluid based on glucose level range is depicted in a flowchart. A scaling factor K is defined for lag correction that takes the value from 0 (for no lag correction) to 1 (for full lag correction) (802). For example, let a non-lag corrected glucose value at any time t be G_latest(t), the nominal lag correction amount be G_c(t), and the final lag corrected value be G_lag(t), such that:

$$G\_lag(t)=G\_latest(t)+(KG\_c(t)) \quad \text{(Equation 2)}$$

A moving window of historical glucose sensor data is collected (804). The period of sensor data collection can be on the order of two to three days. In some embodiments, the data includes sensor data from prior sensor wears from the same patient. A time of day probability density function p(tod) of the patient's glucose level based on data in the moving window is defined using a second window size, for example, on the order of two to three hours (806). A normalized glucose variability ratio, Vn(t) is determined (808). An example of a normalized glucose variability ratio is the ratio of glucose standard deviation to glucose mean within the moving window (or other similar metric) that computes variability normalized to the overall value. Other examples of variability aside from standard deviation include the absolute distance between the upper and lower quartile of the glucose level in the moving window. An additional example includes the absolute distance between the median glucose and a percentile (e.g., the tenth percentile) of the glucose in the window. Examples of an overall value aside from mean glucose include the median glucose, the average of a middle range (e.g., the 45$^{th}$ and 55$^{th}$ percentile) glucose values in the window, etc. The normalized glucose variability ratio Vn(t) computed at regular intervals is stored (810). In some embodiments, the regular intervals are on the order of every 2 to 3 days, for example. The latest normalized glucose variability ratio Vn(t) is compared to a predetermined value Vo and the past Vn values (812). Vo is computed a priori from population data.

The value of the scaling factor K is set based upon the time of day probability density function p(tod) (814). At a time of day when the time of day probability density function p(tod) predicts a high probability of low average glucose, or when the variability from the historic window is very low, K is set close to 0. Otherwise, K is set close to 1. For example, the p(tod) can be used to determine the probability of glucose being lower than, e.g., 100 mg/dL (within a 2 to 3 hour window at the current time of day). This probability can be defined as pLow(tod), which takes on the value of 1 when the probability is 100%, and 0 when the probability is 0%. Then, the scaling factor for lag correction can be computed at any time (and given that time of day) using the equation:

$$K(t,tod)=\min(k\text{Low},kN\text{ Var},kR\text{ Var}) \quad \text{(Equation 3)}$$

where kLow represents the gain that mitigates against historic glucose-based, predicted low glucose (kLow=1−pLow(tod)), kNVar represents the gain that mitigates against Vo normalized glucose variability (kNVar=Vn(t)No(t)), and kRVar represents the gain that mitigates against past Vn normalized glucose variability (kRVar=Vn(t)/max([Vn(t−N), Vn(t−N+1), . . . , Vn(t−2), Vn(t−1)])). In this example, N can be on the order of 1 week. Hence, K(t,tod) is the smallest of the three values, kLow, kNVar, kRVar, computed at any time t. The final lag corrected values are computed using Equation 2 based on the scaling factor computed in Equation 3 (816).

Various other modifications and alterations in the structure and method of operation of the embodiments of the present disclosure will be apparent to those skilled in the art without departing from the scope and spirit of the present disclosure. Although the present disclosure has been described in connection with certain embodiments, it should be understood that the present disclosure as claimed should not be unduly limited to such embodiments. It is intended that the following claims define the scope of the present disclosure and that structures and methods within the scope of these claims and their equivalents be covered thereby.

What is claimed is:

1. A method for lag correction of sensor data from a glucose sensor, comprising:
   receiving sensor data from a glucose sensor, the sensor data including historical glucose sensor data over a plurality of intervals;
   determining a variability of the historical glucose sensor data over each of the plurality of intervals;
   comparing the variability of the historical glucose sensor data of a recent interval of the plurality of intervals to at least one prior variability determined from prior intervals of the plurality of intervals;
   calculating a noise metric of the historical glucose sensor data of the recent interval of the plurality of intervals;
   setting an amount of lag correction based on the noise metric and at least one of the variability of the recent interval and the at least one prior variability; and
   computing lag corrected values based on the amount of lag correction.

2. The method of claim 1, further comprising:
   defining a probability density function of the historical glucose sensor data over at least a portion of one of the plurality of intervals; and
   setting the amount of lag correction based further on the probability density function of the historical glucose sensor data.

3. The method of claim 1, wherein the variability of the historical glucose sensor data is measured using a normalized glucose variability ratio.

4. The method of claim 1, wherein the variability is determined based on at least one of standard deviation or absolute distance between an upper and a lower quartile of the historical glucose sensor data over one or more of the plurality of intervals.

5. The method of claim 1, further comprising:
   comparing the variability of the historical glucose sensor data of the recent interval to a variability determined from population data.

6. The method of claim 1, wherein setting the amount of lag correction further includes relating the lag corrected values to a scaling factor based on an equation:

$$G\text{lag}(t)=G\text{ latest}(t)+(K\ G\ c(t))$$

wherein K represents the scaling factor, G latest(t) represents a non-lag corrected glucose value at time t, G c(t) represents a nominal lag correction amount at time t, and G lag(t) represents the lag corrected value at time t.

7. The method of claim 1, wherein the amount of lag correction is within a range from zero to one, and wherein zero corresponds to no lag correction and one corresponds to full lag correction.

8. The method of claim 1, wherein each of the plurality of intervals is at least two days.

9. The method of claim 1, wherein at least a portion of one of the plurality of intervals is three hours or less.

10. A system for lag correction of sensor data from a glucose sensor, comprising:
- a processor; and
- a memory coupled to the processor, the memory storing processor executable instructions to:
- receive sensor data from the glucose sensor, the sensor data including historical glucose sensor data over a plurality of intervals;
- determine a variability of the historical glucose sensor data over each of the plurality of intervals;
- compare the variability of the historical glucose sensor data of a recent interval of the plurality of intervals to at least one prior variability determined from prior intervals of the plurality of intervals;
- calculate a noise metric of the historical glucose sensor data of the recent interval of the plurality of intervals;
- set an amount of lag correction based on the noise metric and at least one of the variability of the recent interval and the at least one prior variability; and
- compute lag corrected values based on the amount of lag correction.

11. The system of claim 10, further comprising instructions to:
- define a probability density function of the historical glucose sensor data over at least a portion of one of the plurality of intervals; and
- set the amount of lag correction based further on the probability density function of the historical glucose sensor data.

12. The system of claim 10, wherein the variability of the historical glucose sensor data is measured using a normalized glucose variability ratio.

13. The system of claim 10, wherein the variability is determined based on at least one of standard deviation or absolute distance between an upper and a lower quartile of the historical glucose sensor data over one or more of the plurality of intervals.

14. The system of claim 10, further comprising instructions to:
- compare the variability of the historical glucose sensor data of the recent interval to a variability determined from population data.

15. The system of claim 10, wherein setting the amount of lag correction further includes relating the lag corrected values to a scaling factor based on an equation:

$$G\mathrm{lag}(t) = G\ \mathrm{latest}(t) + (K\ G\ c(t))$$

wherein K represents the scaling factor, G latest(t) represents a non-lag corrected glucose value at time t, G c(t) represents a nominal lag correction amount at time t, and G lag(t) represents the lag corrected value at time t.

16. The system of claim 10, wherein the amount of lag correction is within a range from zero to one, and wherein zero corresponds to no lag correction and one corresponds to full lag correction.

17. The system of claim 10, wherein each of the plurality of intervals is at least two days.

18. The system of claim 10, wherein at least a portion of one of the plurality of intervals is three hours or less.

19. A computer program product stored on a computer-readable medium comprising executable instructions to perform operations comprising:
- receiving sensor data from a glucose sensor, the glucose sensor including historical glucose sensor data over a plurality of intervals;
- determine a variability of the historical glucose sensor data over each of the plurality of intervals;
- compare the variability of the historical glucose sensor data of a recent interval of the plurality of intervals to at least one prior variability determined from prior intervals of the plurality of intervals;
- calculating a noise metric of the historical glucose sensor data of the recent interval of the plurality of intervals;
- set an amount of lag correction based on the noise metric and at least one of the variability of the recent interval and the at least one prior variability; and
- compute lag corrected values based on the amount of lag correction.

20. The computer program product of claim 19, further comprising instructions to:
- define a probability density function of the historical glucose sensor data over at least a portion of one of the plurality of intervals; and
- set the amount of lag correction based further on the probability density function of the historical glucose sensor data.

21. The computer program product of claim 19, wherein the variability of the historical glucose sensor data is measured using a normalized glucose variability ratio.

22. The computer program product of claim 19, wherein the variability is determined based on at least one of standard deviation or absolute distance between an upper and a lower quartile of the historical glucose sensor data over one or more of the plurality of intervals.

23. The computer program product of claim 19, further comprising instructions to perform operations further comprising:
- comparing the variability of the historical glucose sensor data of the recent interval to a variability determined from population data.

* * * * *